(12) United States Patent
Schuessler et al.

(10) Patent No.: US 10,912,869 B2
(45) Date of Patent: *Feb. 9, 2021

(54) WOUND THERAPY SYSTEM WITH RELATED METHODS THEREFOR

(71) Applicant: Smith & Nephew, Inc., Memphis, TN (US)

(72) Inventors: Wayne Schuessler, St. Louis, MO (US); Ricky A. Sisk, Washington, MO (US)

(73) Assignee: Smith & Nephew, Inc., Memphis, TN (US)

( * ) Notice: Subject to any disclaimer, the term of this patent is extended or adjusted under 35 U.S.C. 154(b) by 283 days.

This patent is subject to a terminal disclaimer.

(21) Appl. No.: 16/036,854

(22) Filed: Jul. 16, 2018

(65) Prior Publication Data

US 2018/0318474 A1 Nov. 8, 2018

Related U.S. Application Data

(60) Continuation-in-part of application No. 15/984,077, filed on May 18, 2018, which is a continuation of
(Continued)

(51) Int. Cl.
*A61M 1/00* (2006.01)
*A61M 39/24* (2006.01)
*A61M 27/00* (2006.01)

(52) U.S. Cl.
CPC ........ *A61M 1/0017* (2014.02); *A61M 1/0001* (2013.01); *A61M 1/005* (2014.02);
(Continued)

(58) Field of Classification Search
CPC .. A61M 1/0017; A61M 1/0033; A61M 1/005; A61M 1/0052; A61M 1/0001;
(Continued)

(56) References Cited

U.S. PATENT DOCUMENTS

| 730,062 A | 6/1903 | Widmer |
| 2,468,445 A | 4/1949 | Hurst |

(Continued)

FOREIGN PATENT DOCUMENTS

| AU | 2007201048 | 4/2007 |
| CA | 2 819 475 | 6/2012 |

(Continued)

OTHER PUBLICATIONS

US 6,216,701 B1, 04/2001, Heaton et al. (withdrawn)
(Continued)

*Primary Examiner* — Philip R Wiest
(74) *Attorney, Agent, or Firm* — Knobbe, Martens, Olson & Bear, LLP

(57) ABSTRACT

A portable system for subatmospheric pressure therapy in connection with healing a surgical wound, including a wound dressing dimensioned for positioning relative to a wound bed of a subject and a subatmospheric pressure mechanism dimensioned to be carried or worn by the subject. The subatmospheric pressure mechanism includes a housing having a control unit adapted to draw a vacuum and a canister associated with the housing. The canister has a collection bag disposed therein, which is in fluid communication with the wound dressing to receive exudates from the wound bed. The collection bag is adapted to expand upon receipt of the fluids and has means to release gas from within the collection bag in connection with operation of the control unit. With this arrangement, the canister is attitude independent, i.e., the canister may be positioned on edge, on its side or on its end etc. while still maintaining operation of the control unit. The collection bag may include a hydrophobic vent or material for releasing the gases. In another embodiment, the collection bag comprises a gas permeable
(Continued)

material. The collection bag may include one of pleats or bellows.

5 Claims, 19 Drawing Sheets

Related U.S. Application Data application No. 15/192,605, filed on Jun. 24, 2016, now Pat. No. 9,974,890, which is a division of application No. 14/486,338, filed on Sep. 15, 2014, now Pat. No. 9,375,521, which is a continuation of application No. 13/777,171, filed on Feb. 26, 2013, now Pat. No. 8,834,452, which is a continuation of application No. 12/124,707, filed on May 21, 2008, now Pat. No. 8,414,519, application No. 16/036,854, which is a continuation-in-part of application No. 15/940,529, filed on Mar. 29, 2018, now abandoned, which is a continuation of application No. 14/044,604, filed on Oct. 2, 2013, now Pat. No. 9,931,446, which is a continuation of application No. 13/186,599, filed on Jul. 20, 2011, now Pat. No. 8,551,060, which is a continuation of application No. 12/175,038, filed on Jul. 17, 2008, now Pat. No. 8,007,481, application No. 16/036,854, which is a continuation-in-part of application No. 15/925,481, filed on Mar. 19, 2018, now abandoned, which is a continuation of application No. 14/951,298, filed on Nov. 24, 2015, now Pat. No. 10,004,835, which is a continuation of application No. 13/465,595, filed on May 7, 2012, now Pat. No. 9,205,235, which is a continuation of application No. 12/205,186, filed on Sep. 5, 2008, now Pat. No. 8,177,763.

(52) U.S. Cl.
CPC ........ *A61M 1/0011* (2013.01); *A61M 1/0023* (2013.01); *A61M 1/0033* (2014.02); *A61M 1/0052* (2014.02); *A61M 1/0088* (2013.01); *A61M 27/00* (2013.01); *A61M 39/24* (2013.01); *A61M 2205/21* (2013.01); *A61M 2205/7536* (2013.01); *A61M 2205/8206* (2013.01); *A61M 2205/8293* (2013.01); *A61M 2209/088* (2013.01)

(58) Field of Classification Search
CPC .............. A61M 1/0011; A61M 1/0023; A61M 1/0088; A61M 27/00; A61M 39/24; A61M 2205/21; A61M 2205/7536; A61M 2205/8206; A61M 2205/8293; A61M 2209/088
See application file for complete search history.

(56) References Cited

U.S. PATENT DOCUMENTS

| | | |
|---|---|---|
| 3,367,332 A | 2/1968 | Groves |
| 3,486,504 A | 12/1969 | Austin, Jr. |
| 3,572,340 A | 3/1971 | Lloyd et al. |
| 3,704,709 A | 3/1972 | Sorenson et al. |
| 3,712,298 A | 1/1973 | Snowdon et al. |
| 3,809,086 A | 5/1974 | Schachet et al. |
| 3,866,608 A | 2/1975 | Reynolds et al. |
| 3,874,387 A | 4/1975 | Barbieri |
| 3,980,166 A | 9/1976 | DeFeudis |
| 4,063,556 A | 12/1977 | Thomas et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,203,445 A | 5/1980 | Jessup et al. |
| 4,228,798 A | 10/1980 | Deaton |
| 4,266,545 A | 5/1981 | Moss |
| 4,293,609 A | 10/1981 | Erickson |
| 4,296,748 A | 10/1981 | Kurtz et al. |
| 4,321,020 A | 3/1982 | Mital |
| 4,331,147 A | 5/1982 | Armstrong |
| 4,373,528 A | 2/1983 | Harle |
| 4,376,439 A | 3/1983 | Lauterjung |
| 4,382,441 A | 5/1983 | Svedman |
| 4,402,687 A | 9/1983 | Denty et al. |
| 4,429,693 A | 2/1984 | Blake et al. |
| 4,460,642 A | 7/1984 | Errede et al. |
| 4,524,064 A | 6/1985 | Nambu |
| 4,551,141 A * | 11/1985 | McNeil ............... A61M 1/0019 604/317 |
| 4,569,674 A | 2/1986 | Phillips et al. |
| 4,573,992 A | 3/1986 | Marx |
| 4,578,060 A | 3/1986 | Huck et al. |
| 4,585,397 A | 4/1986 | Crawford et al. |
| 4,604,313 A | 8/1986 | McFarland et al. |
| 4,642,088 A | 2/1987 | Gunter |
| 4,642,093 A | 2/1987 | Harle |
| 4,655,754 A | 4/1987 | Richmond et al. |
| 4,675,010 A | 6/1987 | Siposs et al. |
| 4,706,830 A | 11/1987 | Wareing |
| 4,738,671 A | 4/1988 | Elliott et al. |
| 4,743,232 A | 5/1988 | Kruger |
| 4,747,844 A | 5/1988 | Elliott |
| 4,758,238 A | 7/1988 | Sundblom et al. |
| 4,767,417 A | 8/1988 | Boehringer et al. |
| 4,769,019 A | 9/1988 | Kerwin |
| 4,798,578 A | 1/1989 | Ranford |
| 4,822,346 A | 4/1989 | Elliott |
| 4,826,494 A | 5/1989 | Richmond et al. |
| 4,828,546 A | 5/1989 | McNeil et al. |
| 4,832,299 A | 5/1989 | Gorton et al. |
| 4,840,770 A | 6/1989 | Walz et al. |
| 4,850,964 A | 7/1989 | Cotter |
| 4,865,816 A | 9/1989 | Walz et al. |
| 4,870,975 A | 10/1989 | Cronk et al. |
| 4,889,531 A | 12/1989 | D'Antonio et al. |
| 4,925,447 A | 5/1990 | Rosenblatt |
| 4,950,247 A | 8/1990 | Rosenblatt |
| 4,955,391 A | 9/1990 | Parker et al. |
| 4,969,880 A | 11/1990 | Zamierowski |
| 4,976,694 A | 12/1990 | Schreibman |
| 4,979,944 A | 12/1990 | Luzsicza |
| 4,981,474 A | 1/1991 | Bopp et al. |
| 4,988,344 A | 1/1991 | Reising et al. |
| 4,988,345 A | 1/1991 | Reising |
| 4,990,137 A | 2/1991 | Graham |
| 4,997,438 A | 3/1991 | Nipper |
| 5,002,529 A | 3/1991 | Cunningham |
| 5,002,534 A | 3/1991 | Rosenblatt |
| 5,053,026 A | 10/1991 | Andersen et al. |
| 5,055,198 A | 10/1991 | Shettigar |
| 5,071,104 A | 12/1991 | Witt et al. |
| 5,071,409 A | 12/1991 | Rosenberg |
| 5,073,172 A | 12/1991 | Fell |
| 5,100,395 A | 3/1992 | Rosenberg |
| 5,100,396 A | 3/1992 | Zamierowski |
| 5,106,629 A | 4/1992 | Cartmell et al. |
| 5,112,323 A | 5/1992 | Winkler et al. |
| 5,135,485 A | 8/1992 | Cohen et al. |
| 5,141,503 A | 8/1992 | Sewell, Jr. |
| 5,141,504 A | 8/1992 | Herweck et al. |
| 5,149,325 A | 9/1992 | Telang et al. |
| 5,149,331 A | 9/1992 | Ferdman et al. |
| 5,152,757 A | 10/1992 | Eriksson |
| 5,156,602 A | 10/1992 | Steffler |
| 5,158,533 A | 10/1992 | Strauss et al. |
| 5,160,322 A | 11/1992 | Scheremet et al. |
| 5,176,663 A | 1/1993 | Svedman et al. |
| 5,178,157 A | 1/1993 | Fanlo |
| 5,188,622 A | 2/1993 | Muller et al. |
| 5,192,439 A | 3/1993 | Roth et al. |

(56) References Cited

U.S. PATENT DOCUMENTS

| | | |
|---|---|---|
| 5,195,977 A | 3/1993 | Pollitt |
| 5,219,428 A | 6/1993 | Stern |
| 5,246,353 A | 9/1993 | Sohn |
| 5,254,080 A | 10/1993 | Lindsay |
| 5,261,893 A | 11/1993 | Zamierowski |
| 5,263,922 A | 11/1993 | Sova et al. |
| 5,275,585 A | 1/1994 | Olson |
| 5,342,329 A | 8/1994 | Croquevielle |
| D352,463 S | 11/1994 | Kubo |
| 5,360,445 A | 11/1994 | Goldowsky |
| 5,374,257 A | 12/1994 | Drainville et al. |
| 5,382,244 A | 1/1995 | Telang |
| 5,386,735 A * | 2/1995 | Langdon ............ A61M 1/0001 73/863.23 |
| 5,397,299 A | 3/1995 | Karwoski et al. |
| 5,399,156 A | 3/1995 | Lindsay |
| 5,411,474 A | 5/1995 | Ott et al. |
| 5,458,586 A | 10/1995 | Adiletta |
| D364,679 S | 11/1995 | Heaton et al. |
| 5,466,229 A | 11/1995 | Elson |
| 5,470,585 A | 11/1995 | Gilchrist |
| 5,484,427 A | 1/1996 | Gibbons |
| 5,484,428 A | 1/1996 | Drainville et al. |
| 5,496,299 A | 3/1996 | Felix et al. |
| 5,527,293 A | 6/1996 | Zamierowski |
| 5,536,233 A | 7/1996 | Khouri |
| 5,542,939 A | 8/1996 | Onodera et al. |
| 5,545,151 A | 8/1996 | O'Connor et al. |
| 5,549,584 A | 8/1996 | Gross |
| 5,582,601 A | 12/1996 | Wortrich et al. |
| 5,584,824 A | 12/1996 | Gillette et al. |
| 5,588,958 A | 12/1996 | Cunningham et al. |
| 5,591,297 A | 1/1997 | Ahr |
| 5,599,174 A | 2/1997 | Cook et al. |
| 5,630,855 A | 5/1997 | Lundbaeck |
| 5,636,643 A | 6/1997 | Argenta et al. |
| 5,645,081 A | 7/1997 | Argenta et al. |
| 5,656,027 A | 8/1997 | Ellingboe |
| 5,669,892 A | 9/1997 | Keogh et al. |
| 5,678,564 A | 10/1997 | Lawrence et al. |
| 5,685,214 A | 11/1997 | Neff et al. |
| 5,688,516 A | 11/1997 | Raad et al. |
| 5,693,013 A | 12/1997 | Geuder |
| 5,701,917 A | 12/1997 | Khouri |
| 5,707,173 A | 1/1998 | Cottone et al. |
| 5,733,305 A | 3/1998 | Fleischmann |
| 5,762,638 A | 6/1998 | Shikani et al. |
| 5,776,118 A | 7/1998 | Seifert et al. |
| 5,785,700 A | 7/1998 | Olson |
| 5,787,928 A | 8/1998 | Allen et al. |
| 5,807,359 A | 9/1998 | Bemis et al. |
| 5,809,157 A | 9/1998 | Grumazescu |
| D400,249 S | 10/1998 | Holubar et al. |
| 5,840,049 A | 11/1998 | Tumey et al. |
| 5,876,387 A | 3/1999 | Killian et al. |
| 5,882,743 A | 3/1999 | McConnell |
| D408,625 S | 4/1999 | Barker |
| 5,911,222 A | 6/1999 | Lawrence et al. |
| 5,944,703 A | 8/1999 | Dixon et al. |
| 5,960,837 A | 10/1999 | Cude |
| 5,997,733 A | 12/1999 | Wilbur et al. |
| 6,010,524 A | 1/2000 | Fleischmann |
| 6,010,527 A | 1/2000 | Augustine et al. |
| 6,071,267 A | 6/2000 | Zamierowski |
| 6,075,177 A | 6/2000 | Bahia et al. |
| 6,093,230 A | 7/2000 | Johnson, III et al. |
| 6,099,493 A | 8/2000 | Swisher |
| 6,102,205 A | 8/2000 | Greff et al. |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,152,902 A | 11/2000 | Christian et al. |
| 6,168,758 B1 | 1/2001 | Forsberg et al. |
| 6,174,306 B1 | 1/2001 | Fleischmann |
| 6,180,000 B1 | 1/2001 | Wilbur et al. |
| 6,203,563 B1 | 3/2001 | Fernandez |
| 6,261,276 B1 | 7/2001 | Reitsma |
| D449,891 S | 10/2001 | Moro |
| 6,322,546 B1 | 11/2001 | Steg |
| 6,325,788 B1 | 12/2001 | McKay |
| 6,345,623 B1 | 2/2002 | Heaton et al. |
| 6,348,423 B1 | 2/2002 | Griffiths et al. |
| 6,352,233 B1 | 3/2002 | Barberich |
| D456,514 S | 4/2002 | Brown et al. |
| 6,395,955 B1 | 5/2002 | Roe et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,420,662 B1 | 7/2002 | Ishikawa |
| 6,458,109 B1 | 10/2002 | Henley et al. |
| 6,468,199 B1 | 10/2002 | Satou et al. |
| 6,478,774 B1 | 11/2002 | Balugani et al. |
| 6,488,643 B1 | 12/2002 | Tumey et al. |
| 6,500,112 B1 | 12/2002 | Khouri |
| 6,501,002 B1 | 12/2002 | Roe et al. |
| D469,175 S | 1/2003 | Hall et al. |
| D469,176 S | 1/2003 | Hall et al. |
| 6,520,982 B1 | 2/2003 | Boynton et al. |
| 6,547,255 B1 | 4/2003 | Donaway et al. |
| 6,553,998 B2 | 4/2003 | Heaton et al. |
| D475,132 S | 5/2003 | Randolph |
| D475,134 S | 5/2003 | Randolph |
| 6,557,704 B1 | 5/2003 | Randolph |
| 6,575,333 B1 | 6/2003 | Raboin |
| D477,869 S | 7/2003 | Vijfvinkel |
| D478,659 S | 8/2003 | Hall et al. |
| 6,607,495 B1 | 8/2003 | Skalak et al. |
| 6,620,379 B1 | 9/2003 | Pluk et al. |
| 6,626,891 B2 | 9/2003 | Ohmstede |
| D481,459 S | 10/2003 | Naham |
| 6,635,028 B1 | 10/2003 | Ielpo et al. |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,723,430 B2 | 4/2004 | Kurata et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,820,483 B1 | 11/2004 | Beckerman |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,868,739 B1 | 3/2005 | Krivitski et al. |
| 6,885,116 B2 | 4/2005 | Knirck et al. |
| D504,953 S | 5/2005 | Ryan |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,955,664 B2 | 10/2005 | D'Antonio |
| 6,960,181 B2 | 11/2005 | Stevens |
| 6,979,324 B2 | 12/2005 | Bybordi et al. |
| D516,217 S | 2/2006 | Brown et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,037,254 B2 | 5/2006 | O'Connor et al. |
| 7,052,167 B2 | 5/2006 | Vanderschuit |
| D522,657 S | 6/2006 | Murphy et al. |
| 7,066,949 B2 | 6/2006 | Gammons et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |

(56) References Cited

U.S. PATENT DOCUMENTS

| | | |
|---|---|---|
| 7,144,390 B1 | 12/2006 | Hanningan et al. |
| 7,153,294 B1 | 12/2006 | Farrow |
| 7,169,151 B1 | 1/2007 | Lytinas |
| 7,182,758 B2 | 2/2007 | McCraw |
| D537,944 S | 3/2007 | Eda et al. |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,240,676 B2 | 7/2007 | Rutter |
| D548,347 S | 8/2007 | Ichino et al. |
| D551,578 S | 9/2007 | Kuriger et al. |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| D580,285 S | 11/2008 | Hendrickson et al. |
| D581,042 S | 11/2008 | Randolph et al. |
| D581,522 S | 11/2008 | Randolph et al. |
| D585,137 S | 1/2009 | Onoda et al. |
| 7,503,910 B2* | 3/2009 | Adahan ............... A61M 1/0092 604/319 |
| D590,934 S | 4/2009 | Randolph et al. |
| 7,524,315 B2 | 4/2009 | Blott et al. |
| D593,676 S | 6/2009 | Locke et al. |
| D594,114 S | 6/2009 | Locke et al. |
| 7,553,306 B1 | 6/2009 | Hunt et al. |
| 7,569,742 B2 | 8/2009 | Haggstrom et al. |
| D602,582 S | 10/2009 | Pidgeon et al. |
| D602,583 S | 10/2009 | Pidgeon et al. |
| D602,584 S | 10/2009 | Pidgeon et al. |
| 7,604,610 B2 | 10/2009 | Shener et al. |
| 7,611,500 B1 | 11/2009 | Lina et al. |
| 7,615,036 B2 | 11/2009 | Joshi et al. |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| D617,094 S | 6/2010 | Pidgeon et al. |
| D617,461 S | 6/2010 | Kaushal et al. |
| 7,731,702 B2 | 6/2010 | Bybordi et al. |
| 7,758,554 B2 | 7/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,794,450 B2 | 9/2010 | Blott et al. |
| D625,801 S | 10/2010 | Pidgeon et al. |
| 7,837,673 B2 | 11/2010 | Vogel |
| 7,846,141 B2 | 12/2010 | Weston |
| D630,313 S | 1/2011 | Pidgeon et al. |
| D630,725 S | 1/2011 | Pidgeon et al. |
| 7,862,339 B2 | 1/2011 | Mulligan |
| 7,896,856 B2 | 3/2011 | Petrosenko et al. |
| 7,909,805 B2 | 3/2011 | Weston |
| 7,927,318 B2 | 4/2011 | Risk, Jr. et al. |
| 7,964,766 B2 | 6/2011 | Blott et al. |
| 7,998,125 B2 | 8/2011 | Weston |
| 8,007,481 B2* | 8/2011 | Schuessler .......... A61M 1/0023 604/313 |
| 8,021,348 B2 | 9/2011 | Risk, Jr. et al. |
| 8,048,046 B2 | 11/2011 | Hudspeth et al. |
| 8,061,360 B2 | 11/2011 | Locke et al. |
| 8,062,272 B2 | 11/2011 | Weston |
| 8,080,702 B2 | 12/2011 | Blott et al. |
| 8,100,873 B2 | 1/2012 | Jaeb et al. |
| 8,162,909 B2 | 4/2012 | Blott et al. |
| 8,172,817 B2 | 5/2012 | Michaels et al. |
| 8,177,763 B2* | 5/2012 | Wiesner ............... A61M 1/0049 604/313 |
| 8,235,972 B2 | 8/2012 | Adahan |
| 8,240,470 B2 | 8/2012 | Pidgeon et al. |
| 8,246,607 B2 | 8/2012 | Karpowicz et al. |
| 8,257,327 B2 | 9/2012 | Blott et al. |
| 8,257,328 B2 | 9/2012 | Augustine et al. |
| 8,267,909 B2 | 9/2012 | Clementi et al. |
| 8,267,918 B2 | 9/2012 | Johnson et al. |
| 8,294,586 B2 | 10/2012 | Pidgeon et al. |
| 8,308,714 B2 | 11/2012 | Weston et al. |
| 8,323,264 B2 | 12/2012 | Weston et al. |
| 8,333,744 B2 | 12/2012 | Hartwell et al. |
| 8,348,910 B2 | 1/2013 | Blott et al. |
| 8,372,049 B2 | 2/2013 | Jaeb et al. |
| 8,372,050 B2 | 2/2013 | Jaeb et al. |
| 8,414,519 B2* | 4/2013 | Hudspeth ............ A61M 1/0017 604/10 |
| 8,444,392 B2 | 5/2013 | Turner et al. |
| 8,460,255 B2 | 6/2013 | Joshi et al. |
| 8,494,349 B2 | 7/2013 | Gordon |
| 8,535,283 B2 | 9/2013 | Heaton et al. |
| 8,551,060 B2* | 10/2013 | Schuessler .......... A61M 1/0023 604/313 |
| 8,551,061 B2 | 10/2013 | Hartwell et al. |
| 8,556,871 B2 | 10/2013 | Mormino et al. |
| 8,569,566 B2 | 10/2013 | Blott et al. |
| 8,617,129 B2 | 12/2013 | Hartwell |
| 8,622,981 B2 | 1/2014 | Hartwell et al. |
| 8,641,691 B2 | 2/2014 | Fink et al. |
| 8,652,111 B2 | 2/2014 | Pratt et al. |
| 8,679,079 B2 | 3/2014 | Heaton et al. |
| 8,747,376 B2 | 6/2014 | Locke et al. |
| 8,771,259 B2 | 7/2014 | Karpowicz et al. |
| 8,814,840 B2 | 8/2014 | Evans et al. |
| 8,814,841 B2 | 8/2014 | Hartwell |
| 8,821,458 B2 | 9/2014 | Locke et al. |
| 8,827,983 B2 | 9/2014 | Braga et al. |
| 8,834,452 B2* | 9/2014 | Hudspeth ............ A61M 1/0088 604/543 |
| 8,843,327 B2 | 9/2014 | Vernon-Harcourt et al. |
| 8,845,603 B2 | 9/2014 | Middleton et al. |
| 8,864,748 B2 | 10/2014 | Coulthard et al. |
| 8,974,429 B2 | 3/2015 | Gordon et al. |
| 9,019,681 B2 | 4/2015 | Locke et al. |
| 9,050,399 B2 | 6/2015 | Hartwell |
| 9,205,183 B2 | 12/2015 | Hartwell et al. |
| 9,205,235 B2* | 12/2015 | Wiesner ............... A61M 1/0049 |
| 9,211,486 B2 | 12/2015 | Locke et al. |
| 9,227,000 B2 | 1/2016 | Fink et al. |
| 9,272,078 B2 | 3/2016 | Jaeb et al. |
| 9,320,838 B2 | 4/2016 | Hartwell et al. |
| 9,375,521 B2* | 6/2016 | Hudspeth ............ A61M 1/0052 |
| 9,408,954 B2 | 8/2016 | Gordon et al. |
| 9,415,145 B2 | 8/2016 | Braga et al. |
| 9,561,312 B2 | 2/2017 | Heaton et al. |
| 9,636,440 B2 | 5/2017 | Weston et al. |
| 9,642,955 B2 | 5/2017 | Fink et al. |
| D802,744 S | 11/2017 | Bjelovuk et al. |
| D813,374 S | 3/2018 | Bjelovuk et al. |
| 9,931,446 B2* | 4/2018 | Schuessler .......... A61M 1/0023 |
| 9,976,890 B2 | 5/2018 | Schollenberger et al. |
| 10,004,835 B2* | 6/2018 | Wiesner ............... A61M 1/0049 |
| 10,130,526 B2 | 11/2018 | Fink et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0026160 A1 | 2/2002 | Takahashi et al. |
| 2002/0143286 A1 | 10/2002 | Tumey |
| 2002/0145012 A1 | 10/2002 | Ho |
| 2002/0151836 A1 | 10/2002 | Burden |

(56) References Cited

U.S. PATENT DOCUMENTS

| | | |
|---|---|---|
| 2002/0156464 A1 | 10/2002 | Blischak et al. |
| 2003/0065292 A1 | 4/2003 | Darouiche |
| 2003/0093041 A1 | 5/2003 | Risk, Jr. et al. |
| 2003/0097100 A1 | 5/2003 | Watson |
| 2003/0101826 A1 | 6/2003 | Neubert |
| 2003/0163101 A1 | 8/2003 | Say |
| 2003/0164600 A1 | 9/2003 | Dunn et al. |
| 2003/0181850 A1 | 9/2003 | Diamond et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2003/0235635 A1 | 12/2003 | Fong et al. |
| 2004/0001767 A1 | 1/2004 | Peters et al. |
| 2004/0006321 A1 | 1/2004 | Cheng et al. |
| 2004/0030304 A1 | 2/2004 | Hunt et al. |
| 2004/0039415 A1 | 2/2004 | Zamierowski |
| 2004/0054338 A1* | 3/2004 | Bybordi ............... A61M 27/00 604/313 |
| 2004/0064132 A1 | 4/2004 | Boehringer et al. |
| 2004/0087918 A1 | 5/2004 | Johnson, III et al. |
| 2004/0093026 A1 | 5/2004 | Weidenhagen et al. |
| 2004/0102743 A1 | 5/2004 | Walker |
| 2004/0116551 A1 | 6/2004 | Terry |
| 2004/0122383 A1 | 6/2004 | Romano et al. |
| 2004/0122434 A1 | 6/2004 | Argenta et al. |
| 2004/0153029 A1 | 8/2004 | Blischak et al. |
| 2004/0167482 A1 | 8/2004 | Watson |
| 2004/0180093 A1 | 9/2004 | Burton et al. |
| 2004/0193218 A1 | 9/2004 | Butler |
| 2004/0233631 A1 | 11/2004 | Lord |
| 2004/0241213 A1 | 12/2004 | Bray |
| 2004/0243073 A1 | 12/2004 | Lockwood et al. |
| 2004/0260230 A1 | 12/2004 | Randolph |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0124966 A1 | 6/2005 | Karpowicz et al. |
| 2005/0144711 A1 | 7/2005 | Valadez et al. |
| 2005/0166683 A1 | 8/2005 | Krivitski et al. |
| 2005/0177190 A1 | 8/2005 | Zamierowski |
| 2005/0182445 A1 | 8/2005 | Zamierowski |
| 2005/0187528 A1 | 8/2005 | Berg |
| 2005/0209560 A1 | 9/2005 | Boukhny et al. |
| 2005/0222527 A1 | 10/2005 | Miller et al. |
| 2005/0248045 A1 | 11/2005 | Anthony |
| 2005/0261643 A1 | 11/2005 | Bybordi et al. |
| 2006/0009744 A1 | 1/2006 | Erdman et al. |
| 2006/0015087 A1 | 1/2006 | Risk, Jr. et al. |
| 2006/0029675 A1 | 2/2006 | Ginther |
| 2006/0039742 A1 | 2/2006 | Cable, Jr. et al. |
| 2006/0041247 A1 | 2/2006 | Petrosenko et al. |
| 2006/0059980 A1 | 3/2006 | Matsubara et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0129137 A1 | 6/2006 | Lockwood et al. |
| 2006/0144440 A1 | 7/2006 | Merkle |
| 2006/0149171 A1 | 7/2006 | Vogel et al. |
| 2006/0280650 A1 | 12/2006 | Wong et al. |
| 2007/0014837 A1 | 1/2007 | Johnson et al. |
| 2007/0016152 A1 | 1/2007 | Karpowicz et al. |
| 2007/0021697 A1 | 1/2007 | Ginther et al. |
| 2007/0027414 A1 | 2/2007 | Hoffman et al. |
| 2007/0027433 A1 | 2/2007 | Garcia et al. |
| 2007/0032741 A1 | 2/2007 | Hibner et al. |
| 2007/0032754 A1 | 2/2007 | Walsh |
| 2007/0032755 A1 | 2/2007 | Walsh |
| 2007/0032763 A1 | 2/2007 | Vogel |
| 2007/0032778 A1 | 2/2007 | Heaton et al. |
| 2007/0055209 A1 | 3/2007 | Patel et al. |
| 2007/0078444 A1 | 4/2007 | Larsson |
| 2007/0118096 A1 | 5/2007 | Smith et al. |
| 2007/0135779 A1 | 6/2007 | Lalomia et al. |
| 2007/0141128 A1 | 6/2007 | Blott et al. |
| 2007/0179460 A1 | 8/2007 | Adahan |
| 2007/0180904 A1 | 8/2007 | Gao |
| 2007/0219513 A1 | 9/2007 | Lina et al. |
| 2007/0219532 A1 | 9/2007 | Karpowicz et al. |
| 2007/0219535 A1 | 9/2007 | Phung et al. |
| 2007/0233022 A1 | 10/2007 | Henley et al. |
| 2007/0244451 A1 | 10/2007 | Romano et al. |
| 2007/0260226 A1 | 11/2007 | Jaeb et al. |
| 2008/0011667 A1 | 1/2008 | Ruschke |
| 2008/0015526 A1 | 1/2008 | Reiner et al. |
| 2008/0033400 A1 | 2/2008 | Holper et al. |
| 2008/0051708 A1 | 2/2008 | Kumar et al. |
| 2008/0071234 A1 | 3/2008 | Kelch et al. |
| 2008/0071235 A1 | 3/2008 | Locke et al. |
| 2008/0082040 A1 | 4/2008 | Kubler et al. |
| 2008/0082077 A1 | 4/2008 | Williams |
| 2008/0108977 A1 | 5/2008 | Heaton et al. |
| 2008/0125697 A1 | 5/2008 | Gao |
| 2008/0125698 A1 | 5/2008 | Gerg et al. |
| 2008/0132855 A1 | 6/2008 | Romano et al. |
| 2008/0183233 A1 | 7/2008 | Koch et al. |
| 2008/0200905 A1 | 8/2008 | Heaton et al. |
| 2008/0234641 A1 | 9/2008 | Locke et al. |
| 2008/0243096 A1 | 10/2008 | Svedman |
| 2008/0281281 A1 | 11/2008 | Meyer et al. |
| 2009/0005746 A1 | 1/2009 | Nielsen et al. |
| 2009/0043268 A1 | 2/2009 | Eddy et al. |
| 2009/0101219 A1 | 4/2009 | Martini et al. |
| 2009/0125004 A1 | 5/2009 | Shen et al. |
| 2009/0157016 A1 | 6/2009 | Adahan |
| 2009/0204049 A1 | 8/2009 | Lee |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254066 A1 | 10/2009 | Heaton |
| 2009/0275922 A1 | 11/2009 | Coulthard et al. |
| 2009/0299251 A1 | 12/2009 | Buan |
| 2009/0299306 A1 | 12/2009 | Buan |
| 2009/0312725 A1 | 12/2009 | Braga |
| 2010/0022990 A1 | 1/2010 | Karpowicz et al. |
| 2010/0030132 A1 | 2/2010 | Niezgoda et al. |
| 2010/0036333 A1 | 2/2010 | Schenk, III et al. |
| 2010/0042059 A1 | 2/2010 | Pratt et al. |
| 2010/0121257 A1 | 5/2010 | King |
| 2010/0126268 A1 | 5/2010 | Baily et al. |
| 2010/0145289 A1 | 6/2010 | Line et al. |
| 2010/0211030 A1 | 8/2010 | Turner et al. |
| 2010/0268179 A1 | 10/2010 | Kelch et al. |
| 2010/0280435 A1 | 11/2010 | Raney et al. |
| 2010/0280536 A1 | 11/2010 | Hartwell |
| 2010/0305490 A1 | 12/2010 | Coulthard et al. |
| 2010/0324510 A1 | 12/2010 | Andresen et al. |
| 2011/0028918 A1 | 2/2011 | Hartwell |
| 2011/0054421 A1 | 3/2011 | Hartwell |
| 2011/0054810 A1 | 3/2011 | Turner |
| 2011/0063117 A1 | 3/2011 | Turner |
| 2011/0066110 A1 | 3/2011 | Fathallah et al. |
| 2011/0077605 A1 | 3/2011 | Karpowicz et al. |
| 2011/0092958 A1 | 4/2011 | Jacobs |
| 2011/0112493 A1 | 5/2011 | Koch et al. |
| 2011/0130712 A1 | 6/2011 | Topaz |
| 2011/0172615 A2 | 7/2011 | Greener |
| 2011/0172616 A1 | 7/2011 | Hartwell et al. |
| 2011/0251569 A1 | 10/2011 | Turner et al. |
| 2011/0276017 A1 | 11/2011 | Schuessler et al. |
| 2011/0295220 A1 | 12/2011 | Heaton et al. |
| 2011/0313375 A1 | 12/2011 | Michaels |
| 2012/0001762 A1 | 1/2012 | Turner et al. |
| 2012/0035560 A1 | 2/2012 | Eddy et al. |
| 2012/0041399 A1 | 2/2012 | Blott et al. |
| 2013/0090613 A1 | 4/2013 | Kelch et al. |
| 2013/0090615 A1 | 4/2013 | Jaeb et al. |
| 2013/0102979 A1 | 4/2013 | Coulthard et al. |
| 2013/0116635 A1 | 5/2013 | Fleischmann |

(56) References Cited

U.S. PATENT DOCUMENTS

| | | |
|---|---|---|
| 2013/0138054 A1 | 5/2013 | Fleischmann |
| 2013/0144235 A1 | 6/2013 | Augustine et al. |
| 2013/0338614 A1 | 12/2013 | Heaton et al. |
| 2014/0100538 A1 | 4/2014 | Hartwell |
| 2014/0100539 A1 | 4/2014 | Coulthard et al. |
| 2014/0155849 A1 | 6/2014 | Heaton et al. |
| 2014/0163491 A1 | 6/2014 | Schuessler |
| 2014/0188061 A1 | 7/2014 | Locke et al. |
| 2014/0200535 A1 | 7/2014 | Locke et al. |
| 2014/0236106 A1 | 8/2014 | Locke et al. |
| 2014/0276490 A1 | 9/2014 | Locke et al. |
| 2014/0276491 A1 | 9/2014 | Luckemeyer et al. |
| 2014/0276497 A1 | 9/2014 | Robinson |
| 2014/0309601 A1 | 10/2014 | Hall et al. |
| 2014/0320283 A1 | 10/2014 | Lawhorn |
| 2015/0073363 A1 | 3/2015 | Kelch et al. |
| 2015/0073359 A1 | 9/2015 | Hudspeth et al. |
| 2015/0343122 A1 | 12/2015 | Hartwell |
| 2016/0151547 A1 | 6/2016 | Hartwell et al. |
| 2016/0184498 A1 | 6/2016 | Jaeb et al. |
| 2016/0325025 A1 | 11/2016 | Hudspeth et al. |
| 2016/0331877 A1 | 11/2016 | Braga et al. |
| 2018/0104387 A1 | 4/2018 | Braga et al. |
| 2018/0333521 A1 | 11/2018 | Hudspeth et al. |
| 2018/0353352 A1 | 12/2018 | Fink et al. |
| 2019/0009008 A1 | 1/2019 | Hartwell |
| 2019/0060532 A1 | 2/2019 | Hartwell et al. |
| 2019/0099527 A1 | 4/2019 | Schuessler et al. |

FOREIGN PATENT DOCUMENTS

| | | |
|---|---|---|
| CN | 2623320 | 7/2004 |
| DE | 39 16 648 | 9/1990 |
| DE | 41 11 122 A1 | 4/1993 |
| DE | 43 12 852 | 10/1993 |
| DE | 43 06 478 | 9/1994 |
| DE | 295 04 378 U1 | 10/1995 |
| DE | 10 2010 036 405 | 1/2012 |
| EP | 0 020 662 | 7/1984 |
| EP | 0 358 302 | 3/1990 |
| EP | 0 853 950 | 7/1998 |
| EP | 1 476 217 B1 | 3/2008 |
| EP | 2 079 507 | 7/2009 |
| EP | 2 223 711 A1 | 9/2010 |
| EP | 2 248 546 A2 | 11/2010 |
| EP | 2 687 245 | 1/2014 |
| EP | 2 711 034 | 3/2014 |
| EP | 2 305 325 | 4/2014 |
| EP | 2 345 437 | 4/2014 |
| EP | 2 066 365 | 4/2015 |
| GB | 1415096 | 11/1975 |
| GB | 1549756 | 8/1979 |
| GB | 2195255 A | 4/1988 |
| GB | 2235877 A | 3/1991 |
| GB | 2418738 | 4/2006 |
| JP | 2000-202022 | 7/2000 |
| SU | 1762940 | 1/1989 |
| WO | WO 1980/01139 | 6/1980 |
| WO | WO 1980/02182 | 10/1980 |
| WO | WO 1984/01904 | 5/1984 |
| WO | WO 1987/00439 | 1/1987 |
| WO | WO 1989/05133 | 6/1989 |
| WO | WO 1990/11795 | 10/1990 |
| WO | WO 1992/19313 | 11/1992 |
| WO | WO 1996/05873 | 2/1996 |
| WO | WO 1996/19335 | 6/1996 |
| WO | WO 2003/022333 | 3/2003 |
| WO | WO 2003/053346 | 7/2003 |
| WO | WO 2003/057307 | 7/2003 |
| WO | WO 2003/074106 | 9/2003 |
| WO | WO 2003/101508 | 12/2003 |
| WO | WO 2004/060225 | 7/2004 |
| WO | WO 2005/009488 | 2/2005 |
| WO | WO 2005/105179 | 11/2005 |
| WO | WO 2005/123170 | 12/2005 |
| WO | WO 2006/052745 | 5/2006 |
| WO | WO 2006/052839 | 5/2006 |
| WO | WO 2007/087809 | 8/2007 |
| WO | WO 2007/088530 | 8/2007 |
| WO | WO-2007087808 A1 | 8/2007 |
| WO | WO 2008/036344 | 3/2008 |
| WO | WO 2008/036360 | 3/2008 |
| WO | WO 2008/039223 | 4/2008 |
| WO | WO 2008/039314 | 4/2008 |
| WO | WO 2008/048481 | 4/2008 |
| WO | WO 2008/049029 | 4/2008 |
| WO | WO 2008/135997 | 11/2008 |
| WO | WO 2009/004289 | 1/2009 |
| WO | WO 2009/077722 | 6/2009 |
| WO | WO 2009/086580 | 7/2009 |
| WO | WO 2009/124100 | 10/2009 |
| WO | WO 2009/151645 | 12/2009 |
| WO | WO 2010/017484 | 2/2010 |
| WO | WO 2010/039481 | 4/2010 |
| WO | WO 2011/146535 | 11/2011 |
| WO | WO 2014/113504 | 7/2014 |
| WO | WO 2014/107285 | 9/2014 |
| WO | WO 2014/143488 | 9/2014 |

OTHER PUBLICATIONS

US 7,186,244 B1, 03/2007, Hunt et al. (withdrawn)
KCI, "V.A.C. Freedom User's Guide", May 2002, in 16 pages.
Fleischmann, W. et al., "Vacuum Sealing: Indication, Technique and Results", Emr J Orthop Surg Tramatol (1995) 5:37-40, in 5 pages.
International Search Report, re PCT Application No. PCT/US09/46877, dated Jul. 20, 2009.
International Search Report, re PCT Application No. PCT/US09/46890, dated Jul. 23, 2009.
The American Heritage® Science Dictionary, definition of "Evaporation", Copyright © 2005, in 3 pages.
Aubrey, D.A. et al., Treatment of the Perineal Wound after Proctectomy by Intermittent Irrigation, Arch. Surg., Oct. 1984, 119, 1141-1144, in 4 pages.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation), in 14 pages.
Bier, A., Hyperemia as a Therapeutic Agent, Ed. Dr. Gustavus M. Blech, A. Robertson & Co., Chicago 1905.
Arnljots, B. et al., "Irrigation Treatment in Split-Thickness Skin Grafting of Intractable Leg Ulcers," Scand J Plast Reconstr Surg 19: 211-213,1985, in 3 pages.
Bucalo et al. "Inhibition of Cell Proliferation by Chronic Wound Fluid." Wound Repair and Regeneration. Miami, 1993. pp. 181-186.
Chardack, W. et al., "Experimental Studies on Synthetic Substitutes for Skin and Their Use in the Treatment of Burns," Annals of Surgery, vol. 155, No. 1 (127-139), 1962, in 13 pages.
Chariker, M.E. et al, "Effective Management of Incisional and Cutaneous Fistulae with Closed Suction Wound Drainage," Contemporary Surgery. Jun. 1989, pp. 59-63, vol. 34, in 5 pages.
Edlich, R.F., et al., "Evaluation of a New, Improved Surgical Drainage System," The American Journal of Surgery, vol. 149, pp. 295-298, Feb. 1985.
Fleischmann, W., "Vacuum Sealing for Treatment of Problematical Wounds", University Surgical Clinic and Polyclinic—Accident Surgery Department, WundForum Spezial-IHW, 1994, in 4 pages.
Garcia-Rinaldi, R., et al., Improving the Efficiency of Wound Drainage Catheters, Amer. Journ. of Surg., Sep. 1975, 130, 372-373, in 2 pages.
Zivadinovic, G. et al., "Vacuum Therapy in the Treatment of Peripheral Blood Vessels," Conference Papers of the 5th Timok Medical Days, Majdanpek, 1986 (161-164), with translation, in 11 pages.
Health Technology Literature Review, "Vacuum Assisted Closure Therapy for Wound Care", The Medical Advisory Secretariat, Dec. 2004, pp. 3-57, in 57 pages.

(56) References Cited

OTHER PUBLICATIONS

Huntleigh Healthcare, "Negative Pressure Positive Outcomes" WoundASSIST TNP Console and Canister Brochure, 2007, in 6 pages.
Jeter, K. et al., "Managing Draining Wounds and Fistulae: New and Established Methods", Chronic Wound Care, 1990, pp. 240-246, in 7 pages.
KCI V.A.C. ATS—An Advanced Therapy System for Wound Healing, 2007, in 8 pages.
KCI, Inc., V.A.C. Freedom—The Portable and Effective Wound Healing System, 2007, in 8 pages.
KCI, Inc., Acti V.A.C. Therapy System, User Manual, Sep. 2007, in 64 pages.
KCI, Inc., InfoV.A.C. User Manual, Dec. 2006, in 76 pages.
Kostiuchenok, B.M. et al., "The Vacuum Effect in the Surgical Treatment of Purulent Wounds," Russian Journal: Vestnik Khirurgii, Sep. 1986 (18-21), with English translation, in 6 pages.
McLaughlan, James, Sterile Microenvironment for Postoperative Wound Care, The Lancet, pp. 503-504, Sep. 2, 1978.
Meyer, MD. et al., "In Surgery, Medicine and the Specialties A Manual of its Practical Application", Bier's Hyperemic Treatment, Second Revised Edition, W.B. Saunders Company, 1909, in 48 pages.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996), in 10 pages.
Mulder, G.D. et al., "Clinicians' Pocket Guide to Chronic Wound Repair," Wound Healing Publications Second Edition, 1991, in 4 pages.
Photos of 300 mL Canister (with Gel) for ActiV.A.C. believed to be publicly available before Jul. 17, 2008, in 3 pages.
Photos of 1000 mL Canister (with Gel) for V.A.C. ATS believed to be publicly available before Jul. 17, 2008, in 3 pages.
Photos of 300mL Canister (with Gel) for V.A.C. Freedom believed to be publicly available before Jul. 17, 2008, in 3 pages.
Photos of 500 ml Canister (with Gel) for InfoV.A.C. believed to be publicly available before Jul. 17, 2008, in 4 pages.
Renasys EZ System for Negative Wound Therapy, Smith & Nephew announcement, dated Feb. 24, 2009, in 3 pages.
Fujimori, R. M.D. et al., "Sponge Fixation Method for Treatment of Early Scars," From the Department of Dermatology in the Faculty Medicine, Kyoto University, vol. 42, No. 4, Oct. 1968 (322-326), in 5 pages.
Sames, C.P., Sealing of Wounds with Vacuum Drainage, Br. Med. Journ., Nov. 5, 1977, p. 1223, Correspondence.
Sanden, G. M.D. et al., "Staphylococcal Wound Infection in the Pig: Part II. Inoculation, Quantification of Bacteria, and Reproducibility," Annals of Plastic Surgery, vol. 23, No. 3, Sep. 1989, (219-223), in 5 pages.
Stewart, Joanne, Ph.D., World Wide Wounds—Next generation of products for wound management—2002, in 13 pages.
Stoll, S., "Energetic Remedies—Cupping: Healing Within a Vacuum," https://www.suite101.com/article.cfm/ energetic)remedies/74531, Apr. 13, 2005, in 4 pages.
Svedman, P., "A Dressing Allowing Continuous Treatment of a Biosurface," IRCS Medical Science: Biomedical Technology; Clinical Medicine; Surgery and Transplantation, 7, 221 (1979), in 1 page.
Svedman, P. et al., "A Dressing System Providing Fluid Supply and Suction Drainage Used for Continuous or Intermittent Irrigation," Annals of Plastic Surgery, vol. 17, No. 2, Aug. 1986 (125-133).
Svedman, P., "Irrigation Treatment of Leg Ulcers," The Lancet, Sep. 3, 1983 (532-534), in 3 pages.
Svedman, P. et al., "Staphylococcal Wound Infection in the Pig: Part I. Course," Annals of Plastic Surgery, vol. 23, No. 3, Sep. 1989 (212-218), in 7 pages.
Teder, H. et al., "Continuous Wound Irrigation in the Pig," Journal of Investigative Surgery, 1990, vol. 3, pp. 399-407, in 9 pages.
Tribble, D. M.D. "An Improved Sump Drain-Irrigation Device of Simple Construction", Archives of Surgery New York, pp. 511-513, 1972 vol. 105, in 4 pages.
Usupov, Y.N. et al., "Active Wound Drainage," Russian Journal: Vestnik Khirugii, Apr. 1987, (42-45), in 3 pages.
"Vivano—Product application description," Hartmann Vivano, accessed Feb. 28, 2013. URL: http://www.vivanosystem.info/20809.php.
Wu, W.S., et al. Vacuum therapy as an intermediate phase in wound closure: a clinical experience, Eur J Past Surg (2000) 23: 174-177, in 6 pages.
Davydov, Y. et al., "The Bacteriological and Cytological Assessment of Vacuum Therapy of Purulent Wounds", Vestnik Khirurgii, Oct. 1988, (48-52), in 5 pages.
Davydov, Y. et al., "Concepts for Clinical Biological Management of the Wound Process in the Treatment of Purulent Wounds Using Vacuum Therapy," Vestnik Khirugii, Feb. 1991, pp. 132-135, in 4 pages.
Davydov, Y. et al., "Vacuum Therapy in the Treatment of Purulent Lactation Mastitis," Russian Journal: Vesnik Khirurgii, Sep. 1986, with English translation, in 8 pages.
Davydov, Y. et al., "Vacuum Therapy in treatment of Acute Purulent Diseases of Soft Tissues and Purulent Wounds," Vestnik Khirurgii, (Surgeon's Herald), Medicine Publishers, 1986, in 5 pages.
International Preliminary Report on Patentability for Application No. PCT/US2009/046890, dated Mar. 17, 2011, 7 pages.
Written Opinion for Application No. PCT/US2009/046890, dated Jul. 23, 2009, 5 pages.

\* cited by examiner

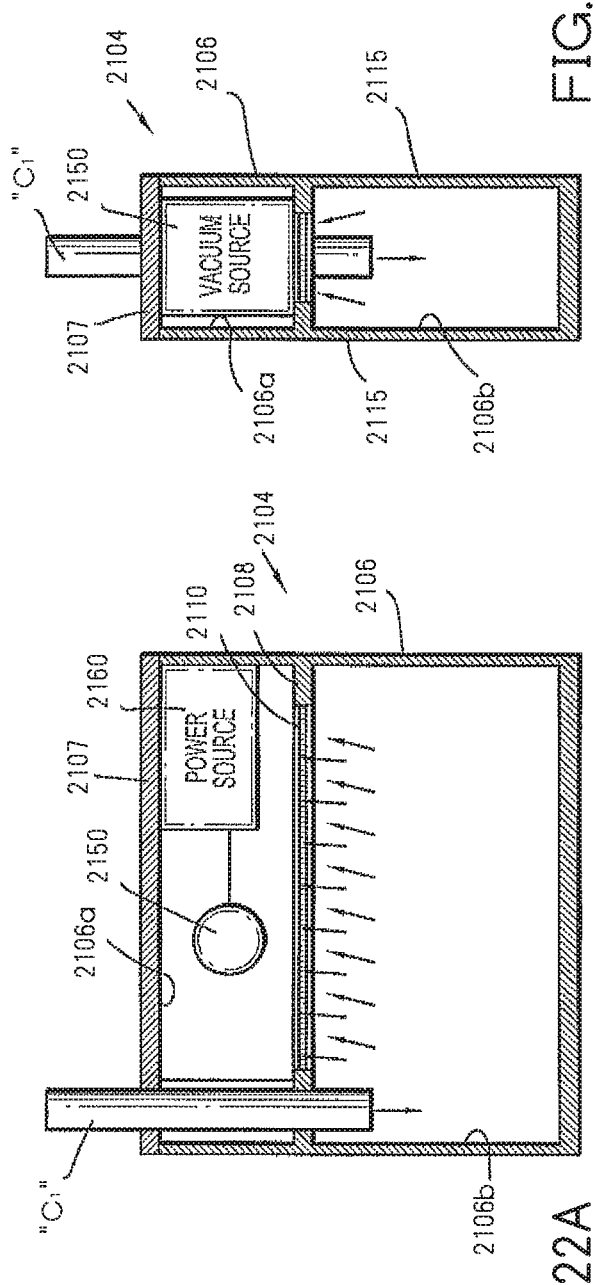
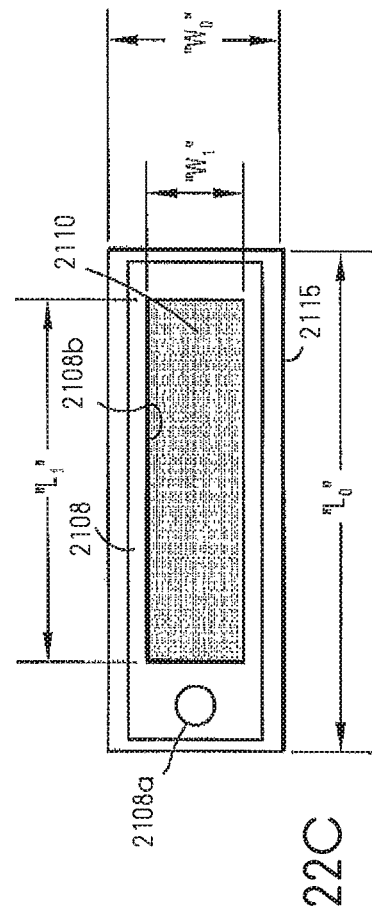
FIG. 22A  FIG. 22B  FIG. 22C

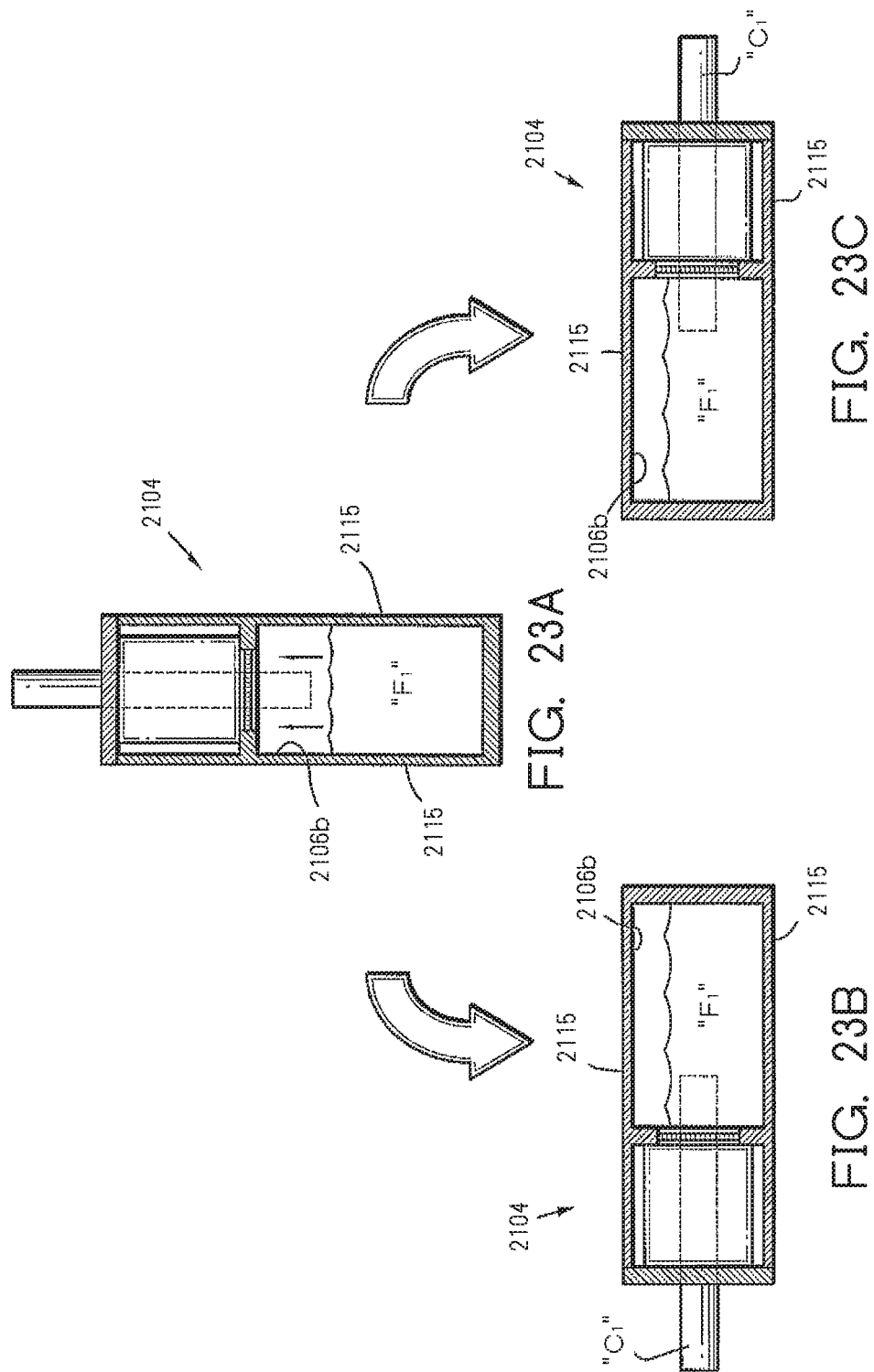

WOUND THERAPY SYSTEM WITH RELATED METHODS THEREFOR

CROSS REFERENCE TO RELATED APPLICATIONS

This application is a continuation-in-part of co-pending U.S. application Ser. No. 15/984,077 filed May 18, 2018, which is a continuation application of U.S. application Ser. No. 15/192,605, filed on Jun. 24, 2016 and issued as U.S. Pat. No. 9,974,890, which is a divisional application of U.S. application Ser. No. 14/486,338, filed on Sep. 15, 2014 and issued as U.S. Pat. No. 9,375,521, which is a continuation of U.S. application Ser. No. 13/777,171, filed on Feb. 26, 2013 and issued as U.S. Pat. No. 8,834,452, which is a continuation of U.S. application Ser. No. 12/124,707, filed May 21, 2008 and issued as U.S. Pat. No. 8,414,519.

This application is also a continuation-in-part of co-pending U.S. application Ser. No. 15/940,529, filed Mar. 29, 2018, which a continuation of U.S. application Ser. No. 14/044,604, filed Oct. 2, 2013 and issued as U.S. Pat. No. 9,931,446, which is a continuation of U.S. application Ser. No. 13/186,599, filed Jul. 20, 2011 and issued as U.S. Pat. No. 8,551,060, which is a continuation of U.S. application Ser. No. 12/175,038, filed on Jul. 17, 2008 and issued as U.S. Pat. No. 8,007,481.

This application is also a continuation-in-part of co-pending U.S. application Ser. No. 15/925,481, filed Mar. 19, 2018, which is a continuation of U.S. application Ser. No. 14/951,298, filed on Nov. 24, 2015 and issued as U.S. patent Ser. No. 10/004,835, which is a continuation of U.S. application Ser. No. 13/465,595, filed on May 7, 2012 and issued as U.S. Pat. No. 9,205,235, which is a continuation of U.S. application Ser. No. 12/205,186, filed on Sep. 5, 2008 and issued as U.S. Pat. No. 8,177,763.

The disclosures of all these prior applications are hereby incorporated herein by reference in their entireties and are to be considered a part of this specification.

BACKGROUND

Technical Field

The present disclosure relates to treating an open wound, and, more specifically, relates to a sub-atmospheric wound therapy system including a portable container adapted to maintain the operation of the system regardless of the orientation or positioning of the container.

The present disclosure relates to treating an open wound, and, more specifically, relates to a wound therapy system including an improved subatmospheric pressure mechanism.

The present disclosure relates to treating an open wound, and, more specifically, relates to a wound therapy system including a portable container having a hydrophobic membrane configured to maximize fluid capacity of the container.

Background of the Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure therapy also known as suction or vacuum therapy has been used in treating and healing wounds. Application of negative pressure, e.g. reduced or subatmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure therapy provides for a wound to be covered to facilitate suction at the wound area. A conduit is introduced through the wound covering to provide fluid communication to an external vacuum source. Atmospheric gas, wound exudates, or other fluids may thus be drawn from the reservoir through the fluid conduit to stimulate healing of the wound. Exudates drawn from the reservoir may be deposited in a collection canister or container.

The systems generally require that the container is maintained in a standing or upright position such that the fluid receiving reservoir within the respective unit may be vented and continue to receive fluid from the patient until the reservoir is full. Accidental tipping or tilting of the bag and/or container may cause the suction to/from the unit to be to be shut-off prior to the fluid receiving reservoir completely filling. This problem is further exaggerated in portable units which may be worn or carried by the subject.

Subatmospheric pressure mechanisms used in wound therapy systems may include a cavity or chamber for receiving the removed exudates, a vacuum source, and a power source. The pressure mechanisms are configured to provide the suction that draws exudates from the wound. Unfortunately. conventional subatmospheric pressure mechanisms have a tendency to develop leaks. Leaks may reduce the efficiency of the system and/or create odor and wetness issues.

SUMMARY OF THE INVENTION

A portable system for subatmospheric pressure therapy in connection with healing a surgical wound includes a wound dressing dimensioned for positioning relative to a wound bed of a subject and a subatmospheric pressure mechanism dimensioned to be carried or worn by the subject. The subatmospheric pressure mechanism includes a housing having a control unit adapted to draw a vacuum and a canister associated with the housing. The canister has a collection bag disposed therein, which is in fluid communication with the wound dressing to receive exudates from the wound bed. The collection bag is adapted to expand upon receipt of the fluids and has means to release gas from within the collection bag in connection with operation of the control unit. With this arrangement, the canister is attitude independent, i.e., the canister may be positioned on edge, on its side or on its end etc. while still maintaining operation of the control unit. The collection bag may include a hydrophobic vent or material for releasing the gases. In another embodiment, the collection bag comprises a gas permeable material. The collection bag may include one of pleats or bellows.

In another embodiment, the portable system for subatmospheric pressure therapy in connection with healing a surgical wound includes a wound dressing dimensioned for positioning relative to a wound bed of a subject and a subatmospheric pressure mechanism dimensioned to be carried or worn by the subject. The subatmospheric pressure mechanism includes a housing having a control unit adapted to draw a vacuum, a container defining an internal chamber in fluid communication with the vacuum and the wound dressing to receive the wound exudates, a plunger received within the internal chamber and movable during actuation of the control unit and a hydrophobic filter associated with the plunger and permitting escape of gas from the container.

In some embodiments, the present disclosure relates to an improved subatmospheric pressure mechanism. A portable system for subatmospheric pressure therapy in connection with healing a surgical wound is provided. The system includes a wound dressing dimensioned for positioning relative to a wound bed of a subject, and a collection canister in fluid communication with the wound dressing. The canister may include a base defining a fluid receiving cavity and having a fluid inlet port and a vacuum port. The fluid inlet port is configured for fluid communication with a wound dressing. A cover is selectively engageable to the base, e.g., in a snap-fit manner. The cover accommodates a control unit and a vent assembly for exhausting the control unit. A seal member is interposed relative to the base and the cover and is adapted to establish and maintain a sealed relationship between these components. At least one of the fluid inlet port and the vacuum port may be configured to receive a cap.

The control unit of the system may include a vacuum source and/or a power source. The vacuum port may also include a hydrophobic membrane. The vent assembly may be recessed relative to the base or cover. The system may further include a divider having a plurality of longitudinal grooves formed on an underside thereof. The divider may further include a channel fluidly communicating the plurality of longitudinal grooves with at least one of the fluid inlet port and the vacuum port. The control unit may be directly connected to the vent assembly.

In some embodiments, the present disclosure is directed to further improvements in negative or subatmospheric pressure therapy. In one embodiment, a subatmospheric pressure therapy system includes self-contained collection canister defining a cavity or chamber for receiving fluid, a vacuum source, and a power source. The vacuum source and fluid receiving cavity may be separated by a hydrophobic filter or membrane. The hydrophobic membrane prevents the aspiration of fluid into the vacuum source. The collection canister of the present disclosure may be placed on its side, tilled or possibly even inverted without affecting operation of the system. This is in contrast to current non-ambulatory fluid collection systems incorporating fluid receptacles which must be in a standing or upright position during operation. In such systems, once a sufficient volume of fluid has been collected in the canister, tipping or tilting of the canister causes the fluid in the canister to cover the hydrophobic membrane. When the hydrophobic membrane is covered by fluid, air is prevented from passing through the membrane, thereby blocking the suction provided by the vacuum source. Without suction, the wound therapy system is ineffective at drawing fluid from the wound. The problem of the hydrophobic membrane becoming covered by fluids may be further exaggerated in portable units which may be worn or carried by the subject.

In one embodiment, a portable system for subatmospheric pressure therapy in connection with healing a surgical wound includes a wound dressing dimensioned for positioning relative to a wound bed of a subject and a collection canister in fluid communication with the wound dressing. The canister includes a first vacuum chamber for drawing a vacuum and a second fluid chamber for collecting fluids removed from the wound dressing under the vacuum. The vacuum chamber may have a vacuum and a power source. The canister further includes a hydrophobic membrane separating the first fluid chamber and the second vacuum chamber. The hydrophobic membrane is dimensioned to span a major portion of the cross-sectional area of the canister. The hydrophobic membrane may be dimensioned to substantially span an internal dimension of the collection canister.

The hydrophobic membrane may include one or more outwardly extending lobes. One of the benefits of these outwardly extending lobes is they may allow for flow in different system attitudes while maintaining the structural integrity of the system. The outwardly extending lobes may be arranged in staggered or symmetrical relation. The hydrophobic membrane may be releasably mountable to the canister, and, may be supported within a divider separating the first vacuum chamber and the second fluid chamber. The divider may include reinforcing ribs for structural support, especially in the areas between the lobes. The divider may constitute a screen or a mesh in the area beneath the hydrophobic membrane to provide additional mechanical support to the membrane. The hydrophobic membrane may be substantially Z-shaped.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 22A is a cross-section said view of the collection canister of the portable wound therapy system of FIG. 21;

FIG. 22B is a cross-sectional end view of the collection canister of FIG. 22A;

FIG. 22C is a top view of the collection canister of FIGS. 22A and 22B with the cover removed;

FIG. 23A is a cross-sectional view of the collection canister of FIGS. 22A-22C, in an upright position;

FIGS. 23B-23C are cross-sectional views illustrating the collection canisters of FIGS. 22A-23A positioned on respective sides of the canister;

DETAILED DESCRIPTION

Figure 1:
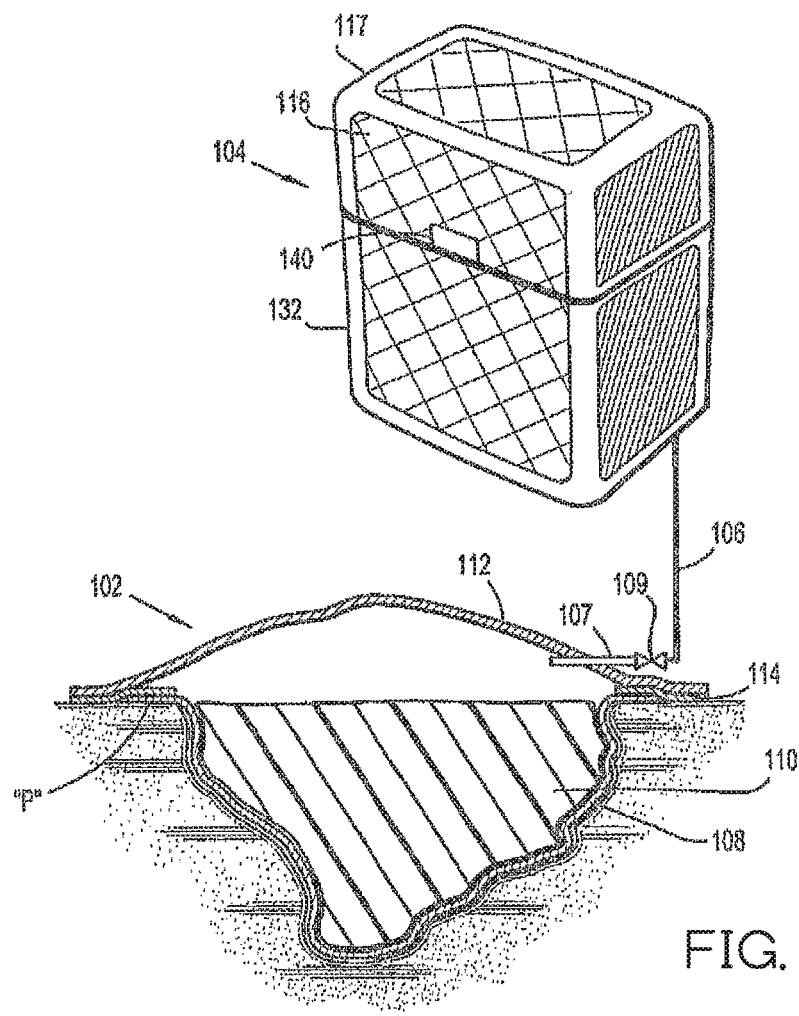
FIG. 1 is a side view in partial cross-section of the portable wound therapy system of the present disclosure illustrating the wound dressing and the subatmospheric pressure mechanism.

Wound Therapy System with Portable Container Apparatus

The wound therapy system of the present disclosure promotes healing of a wound via the use of a wound dressing and a portable subatmospheric pressure mechanism. Generally. The portable subatmospheric pressure mechanism applies subatmospheric pressure to the wound to effectively remove wound fluids or exudates captured by the composite wound dressing. and to increase blood flow to the wound bed and enhance cellular stimulation of epithelial and subcutaneous tissue. The wound therapy system is entirely portable. i.e. it may be worn or carried by the subject such that the subject may be completely ambulatory during the therapy period. The wound therapy system including the subatmospheric pressure mechanism and components thereof may be entirely disposable after a predetermined period of use or may be individually disposable whereby some of the components are reused for a subsequent therapy application.

The wound therapy system of the present disclosure promotes healing of a wound in conjunction with subatmospheric negative pressure therapy. The system may incorporate a variety of wound dressings, subatmospheric pressure sources and pumps, and collection canisters. The attached figures illustrate exemplary embodiments of the present disclosure and are referenced to describe the embodiments depicted therein. Hereinafter, the disclosure will be described by explaining the figures wherein like reference numerals represent like parts throughout the several views.

The following figures illustrate embodiments of the present disclosure and are referenced to describe the embodiments depicted therein. Hereinafter, the disclosure will be described by explaining the figures wherein like reference numerals represent like parts throughout the several views.

Referring initially to FIG. 1, wound therapy system 100 according to the present disclosure is illustrated. Wound therapy system 100 includes composite wound dressing 102 and subatmospheric pressure mechanism 104 in fluid communication with the wound dressing 102 through conduit, identified schematically as reference numeral 106.

Wound dressing 102 may include several components, namely, wound contact layer or member 108, a wound packing member or filler 110 supported by the contact member 108 and outer layer or cover member 112. Wound contact member 108 is adapted to substantially conform to the topography of a wound bed "W". Wound contact member 108 is substantially porous or perforated to permit exudates to pass from the wound bed "W" through the wound contact member 108. The passage of wound exudates through the wound contact member 108 may be unidirectional such that wound exudates do not flow back to the wound bed "W". Unidirectional flow may be encouraged by directional apertures formed in contact member 108 or a lamination of materials having absorption properties differing from those of contact member I 08. A non-adherent material may be selected such that contact member 108 does not tend to cling to wound bed "W" or surrounding material when it is removed. One exemplary material that may be used as a contact member 108 is sold under the trademark XEROFLOW® by Tyco Healthcare Group LP (d/b/a Covidien).

Wound packing member 110 of wound dressing 102 is intended to absorb and transfer wound fluid and exudates. Wound packing member 110 is conformable to assume the shape of any wound bed "W". Wound packing member 110 may be treated with agents such as polyhexamethylene biguanide (PHMB) to decrease the incidence of infection, or other medicants to promote healing of the wound. A suitable wound packing material 110 is the antimicrobial dressing sold under the trademark KERLEX® AMD by Tyco Healthcare Group LP (d/b/a Covidien).

Outer member or wound covering 112 encompasses the perimeter of the wound dressing 102 to surround wound bed "W" and to provide a liquid-tight seal around the perimeter "P" of the wound bed "W". For instance, the sealing mechanism may be any biocompatible adhesive bonded to the perimeter of wound covering 112. Thus, wound covering 112 may act as both a microbial barrier and a fluid barrier to prevent contaminants from entering wound bed "W" and for maintaining the integrity thereof.

Wound covering 112 is typically a flexible material, e.g., resilient or elastomeric, that seals the top of wound dressing 102 to prevent passage of liquids or contamination to and from the wound dressing 102. Wound covering 112 may be formed from a moisture vapor permeable membrane to promote the exchange of oxygen moisture between the wound bed "W" and the atmosphere. A membrane that provides a sufficient moisture vapor transmission rate is a transparent membrane sold under the trade name POLY-SKIN® II by Tyco Healthcare Group LP (d/b/a Covidien). A transparent membrane permits an assessment of wound conditions to be made without requiring removal of the wound covering 112. Alternatively, wound covering 112 may comprise an impermeable membrane or a substantially rigid membrane.

Wound covering 112 may include a port or connector 107 in fluid communication with the interior of wound dressing 102 to facilitate connection of wound dressing 102 to conduit or tubing 106. Conduit 106 defines a fluid flow path leading through wound therapy system 100. Connector 107 may be configured as a rigid or flexible, low-profile component, and may be adapted to receive conduit 106 in a releasable and fluid tight manner. A hollow interior of connector 107 provides fluid communication between conduit 106 and the interior of wound dressing 102. Connector 107 may have a valve 109 built therein, e.g., a one-way valve to permit exudates to flow in one direction only, i.e., away from wound dressing 102 toward subatmospheric pressure mechanism 104. Connector 107 may be provided as a pre-affixed component of wound dressing 102, as a component of conduit 106, or entirely separate and connected thereto by conventional means. Alternatively, connector 107 may be eliminated if other provisions are made for providing fluid communication between wound dressing 102 and conduit 106.

Conduit 106 extends from subatmospheric pressure mechanism 104 to provide fluid communication between the interior of the wound dressing 102 and vacuum source 118. Any suitable conduit may be used including those fabricated from flexible elastomeric or polymeric materials. Conduit 106 may connect to vacuum source 118 or other system components by conventional air tight means such as friction fit, bayonet coupling, or barbed connectors. The conduit connections may be made permanent, or alternatively a quick-disconnect or other releasable means may be used to provide some adjustment flexibility to the apparatus.

Figure 2:
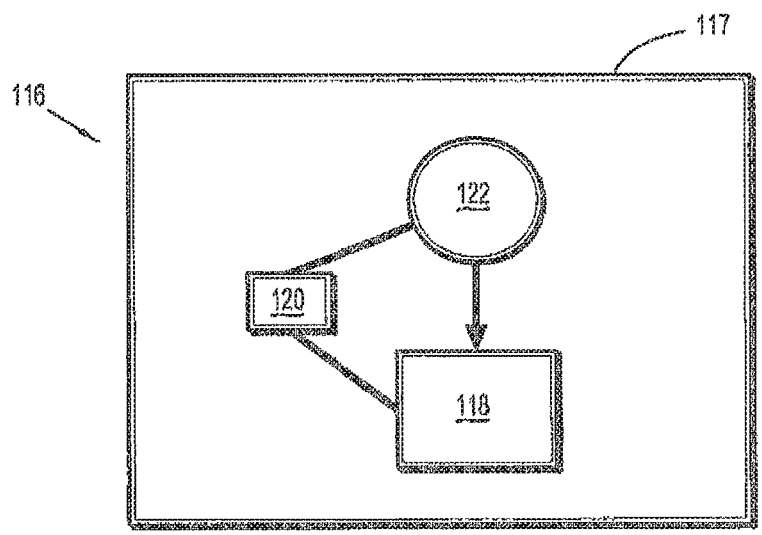
FIG. 2 is a schematic view illustrating the components of the control unit of the subatmospheric pressure mechanism.

Referring now to the schematic diagram of FIG. 2, in conjunction with FIG. 1, control unit 116 of subatmospheric pressure mechanism 104 will be discussed. Control unit 116 includes vacuum source or pump 118 disposed within housing 117, actuator or motor 120 disposed within housing 117 for activating the vacuum source 118 and power source 122 mounted relative to housing 117. Vacuum source or pump 118 generates or otherwise provides negative pressure to wound therapy system 100. Vacuum source or pump 118 may be a pump of the diaphragmatic, peristaltic or bellows type or the like, in which the moving part(s) draw exudates out of the wound bed "W" into the wound dressing 102 by creating areas or zones of decreased pressure e.g., vacuum zones with the wound dressing 100. This area of decreased pressure preferably communicates with the wound bed "W" to facilitate removal of the fluids therefrom and into the absorbent or non-absorbent packing member 110. One suitable peristaltic pump is the Kangaroo Enteral Pump manufactured by Tyco Healthcare Group LP (d/b/a Covidien).

Vacuum source or pump 118 may be a miniature pump or micropump that is biocompatible and adapted to maintain or draw adequate and therapeutic vacuum levels. The vacuum level of subatmospheric pressure achieved may be in the range of about 20 mmHg to about 500 mgHg. In some embodiments. about 75 mmHg and about 125 mmHg is desired or between about 35 mmHg and 75 mmHg may be desired. Vacuum source or pump 118 is actuated by actuator 120 which may be any means known by those skilled in the art, including. for example, AC motors, DC motors, voice coil actuators, solenoids, etc. Actuator 120 may be incorporated within pump 118.

On an exhaust side of vacuum source 118 fluid conduit 106 connects vacuum source 118 to collection canister 132. Conduit 106 may comprise the same material or construction along the entire length of the tubing or may assume an alternate form between vacuum source 118 and canister 132 than between wound dressing 102 and vacuum source 118. In the alternative, it may be separate tubing.

Power source 122 may be disposed within housing 117 or separately mountable to the housing 117. A suitable power source 122 includes alkaline batteries, wet cell batteries. dry cell batteries, nickel cadmium batteries, solar generated means, lithium batteries. NiMH batteries (nickel metal hydride) each of which may be of the disposable or rechargeable variety.

Referring again to FIG. 1, subatmospheric pressure mechanism 104 includes collection canister 132 which collects the exudates removed from the wound bed "W" during therapy through conduit, or tubing, 106. Collection canister 132 is releasably connected to housing 117 of control unit 116. Collection canister 132 may comprise any container suitable for containing wound fluids and is substantially rigid defining an internal chamber 133 in fluid communication with tubing 106. Collection canister 132 may contain an absorbent material to consolidate or contain the wound drainage or debris. In embodiments, at least a portion of collection canister 132 may be transparent to assist in evaluating the color, quality, or quantity of wound exudates. A transparent canister may thus assist in determining the remaining capacity of canister 132 or when the canister 132 should be replaced. In the alternative, collection canister 132 may be relatively flexible.

Figure 3:
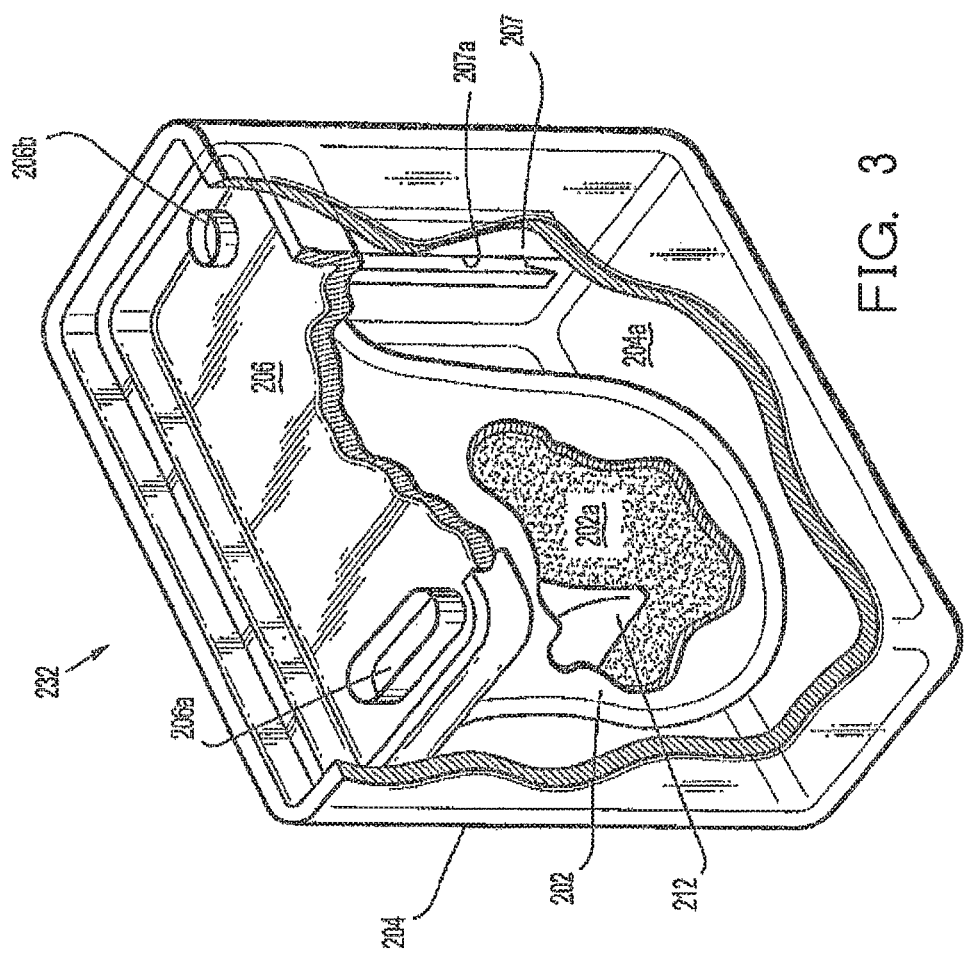
FIG. 3 is a partial cut-away perspective view of an embodiment of a collection canister according to the present disclosure.

Turning now to FIG. 3, an embodiment of a collection canister according to the present disclosure is shown generally as collection canister 232. Collection canister 232 includes a substantially rigid housing 204 defining a chamber 204a for receiving a collection bag 202. A cover 206 is configured t-0 engage container 204 to for a sealed chamber 204a. Alternatively, cover 206 may be integrally formed with housing 117. Cover 206 defines an inlet port 206a and an outlet port 206b. Inlet port 206a is in fluid communication with wound dressing 102 and is configured to receive fluid "F" or exudates therefrom. A check valve 212 may be integrally formed with cover 206. Outlet port 206b is operably connected to vacuum source or pump 118. Outlet port 206 includes an extension 207. Extension 207 extends within chamber 204a of container 204. Extension 207 includes a channel 207a or other suitable configuration to ensure suction continues to be provided to chamber 204a as collection bag 202 expands to fill chamber 204a.

Collection bag 202 includes an expandable cavity 202a configured for receiving fluid "F". Collection bag 202 is constructed with a hydrophobic membrane or other suitable material capable of permitting gases to escape cavity 202a. Alternatively, collection bag 202 may have a hydrophobic vent (not shown). Collection bag 202 is maintained in fluid communication with inlet port 206a. It is envisioned that collection bag 202 may be integrally formed with cover 206.

In operation, suction from pump 118 is provided to chamber 204a of container 204 through outlet port 206b. As a vacuum builds within chamber 204a suction is provided to wound dressing 102 to draw fluid "F" from wound "W". As fluid "F" flows from wound "W" through inlet port 206a into cavity 202a of collection bag 202, any residual air or other gases in the system pass through collection bag 202. Cavity 202a expands to accommodate fluid "F" as the flow into collection bag 202 continues. Check valve 212 prevents fluid "F" from flowing from cavity 202a back towards wound dressing 102. Alternatively, check valve 212 may be formed on a distal end 106b of conduit 106. Collection bag 202 continues to expand as fluid "F" is drawn from wound "W". Channel 207a formed in extension 207 of outlet port 206b is configured to permit the continued flow of suction into chamber 204a, thereby allowing collection bag 202 to expand to fill chamber 204a. Once collection bag 202 and/or chamber 204a is filled, cover 206 may be removed and collection bag 202 may be emptied and/or replaced.

Figure 4:
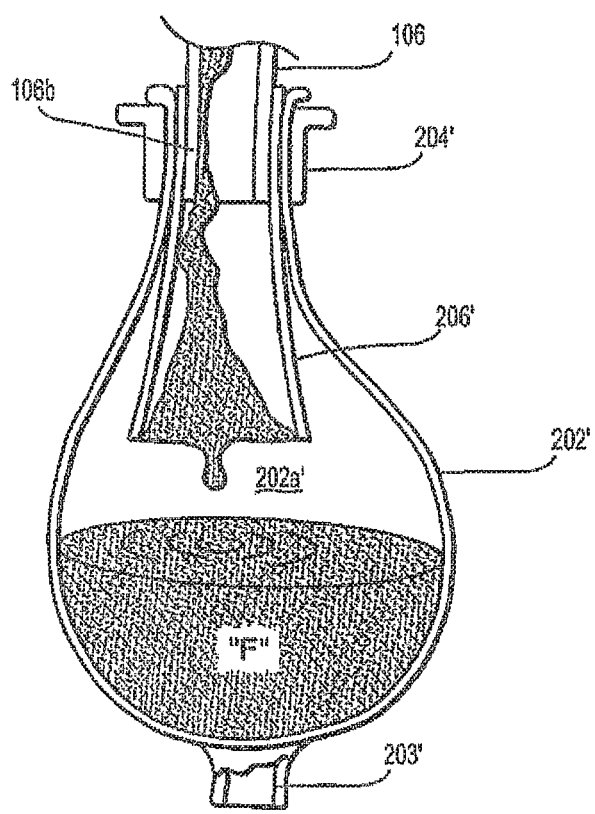
FIG. 4 is a cross-sectional side view of an embodiment of an expandable collection bag according to the present disclosure.

With reference now to FIG. 4, an alternate embodiment of a collection bag for use in collection canister 232 is shown as collection bag 202'. Collection bag 202' defines an expandable cavity 202a' for receiving fluids. A sealing band 204' maintains collection bag 202' in a sealed relationship with patient tube with inlet port 206a of cover 206. A check valve 212' is positioned on a distal end 106b of a conduit 106 to prevent back flow of fluid from collection bag 202' into conduit 106.

Collection bag 202' includes a bulb-shaped container constructed of rubber, polymer or other expandable material. As noted above, collection bag 202' defines an expandable cavity 202a'. Collection bag 202' further includes a hydrophobic plug 203' for releasing gas from within cavity 202a'. As fluid "F" flows from conduit 106 through check valve 212' and into cavity 202a' of collection bag 202', collection bag 202' expands to accommodate the additional fluid. Any gas trapped within cavity 202a' may be vented through hydrophobic plug 203'. Collection bag 202' may be removed from conduit 106 and discarded as necessary. It is envisioned that collection bag 202' may be reused. Collection bag 202' may optionally include a tie, draw string or other suitable closure device for sealing cavity 202a'.

Figure 5:
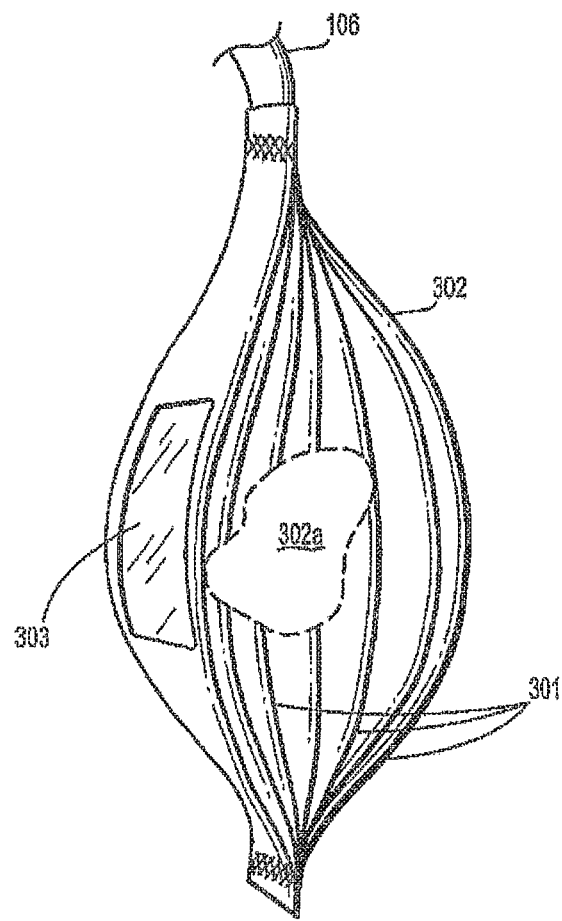
FIG. 5 is a perspective side view of another embodiment of an expandable collection bag according to the present disclosure.

Turning to FIG. 5, an alternate embodiment of a collection bag of the present disclosure is shown generally as collection bag 302. Collection bag 302 includes a pleated container constructed of a hydrophobic material, e.g. TYVEK. This construction permits any air or other gases trapped with the collection system to pass through collection bag 302 while collecting fluid "F" (FIG. 3) therein. Collection bag 302 defines an expandable cavity 302a for receiving fluids In one embodiment, collection bag 302 is preferably configured to expand to fill chamber 204a of collection canister 232. Collection bag 302 may further include a window 303 for viewing the contents of cavity 302a. As fluid enters cavity 302a of collection bag 302, pleats 301 formed in collection bag 302 expand to increase the capacity of cavity 302a and accommodate the additional fluid.

Figure 6:
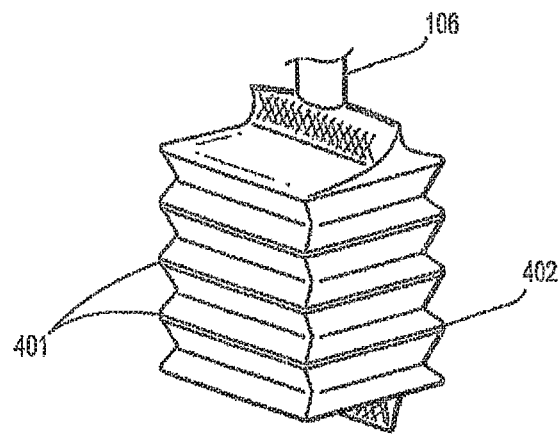
FIG. 6 is a perspective side view of yet another embodiment of an expandable collection bag according to the present disclosure.

With reference now to FIG. 6, another embodiment of a collection bag of the present disclosure is shown as collection bag 402. Collection bag 402 is constructed of hydrophobic material and includes accordion-like folds 401. Folds 401 are configured to expand as collection bag 402 fills with fluid "F" (FIG. 3).

Figure 7:
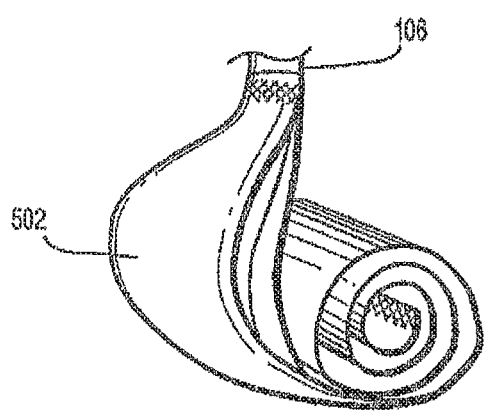
FIG. 7 is a perspective side view of still another embodiment of an expandable collection bag according to the present disclosure.

Turning now to FIG. 7, yet another embodiment of a collection bag is shown generally as collection bag 502. Collection bag 502 is constructed from hydrophobic material that is rolled. Collection bag 502 may include a window (not shown) for viewing the contents therein.

Figure 8:
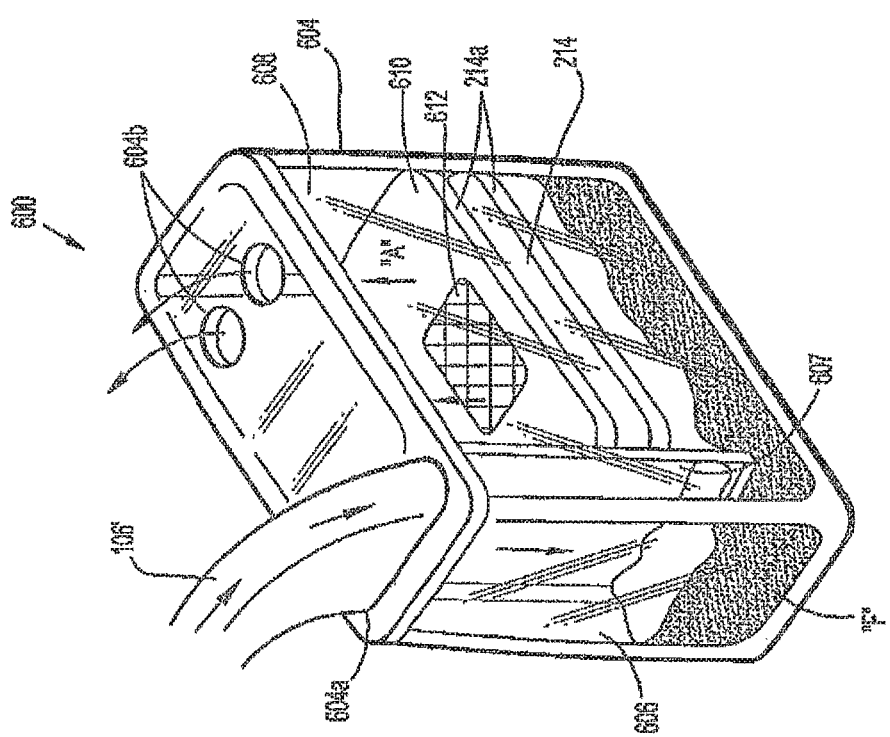
FIG. 8 is an interior perspective view of another embodiment of a collection canister according to the present disclosure.

Turning now to FIG. 8, another embodiment of the present disclosure is shown generally as collection device 600. Collection device 600 includes a container 604 defining a first chamber 606 in fluid communication with a second chamber 608 separated by a divider 607. Container 604 further includes an inlet port 604a in fluid communication with first chamber 606 and one or more outlet ports 604b in fluid communication with the second chamber 608. Inlet port 604a is operably connected to conduit 106'. Conduit 106' may include a check valve (not shown). Outlet ports 604b are operably connected to a source of suction not shown.

A plunger 610 is retained within second chamber 608 of container 604. Plunger 610 is a substantially planar member including a hydrophobic membrane 612 and a seal 214a extending about a perimeter 214 of plunger 610. Plunger 610 is configured to be advanced in the direction of arrow A as suction is applied to outlet ports 604b and air is removed from within second chamber 608. Alternatively, it is envisioned that plunger 610 may be attached to an advancement mechanism, including hydraulic, pneumatic and motorized cylinder, for advancing plunger 610. Movement of plunger 610 towards outlets 604b (direction of arrow "A") creates a vacuum in first chamber 606. The vacuum created in first chamber 606 provides suction to conduit 106'. As plunger 610 is drawn towards outlets 604b fluid "F" fills first and second chamber 606, 608. Residual air trapped within container 604 and/or conduit 106' is exhausted though hydrophobic membrane 612. Once first and second chambers 606, 608 are filled, conduit 106' is disconnected from container 604. Collection device 600 may include a valve or other mechanism (not shown) for draining container 604. Alternatively, collection device 600 may be discarded.

Figure 9:
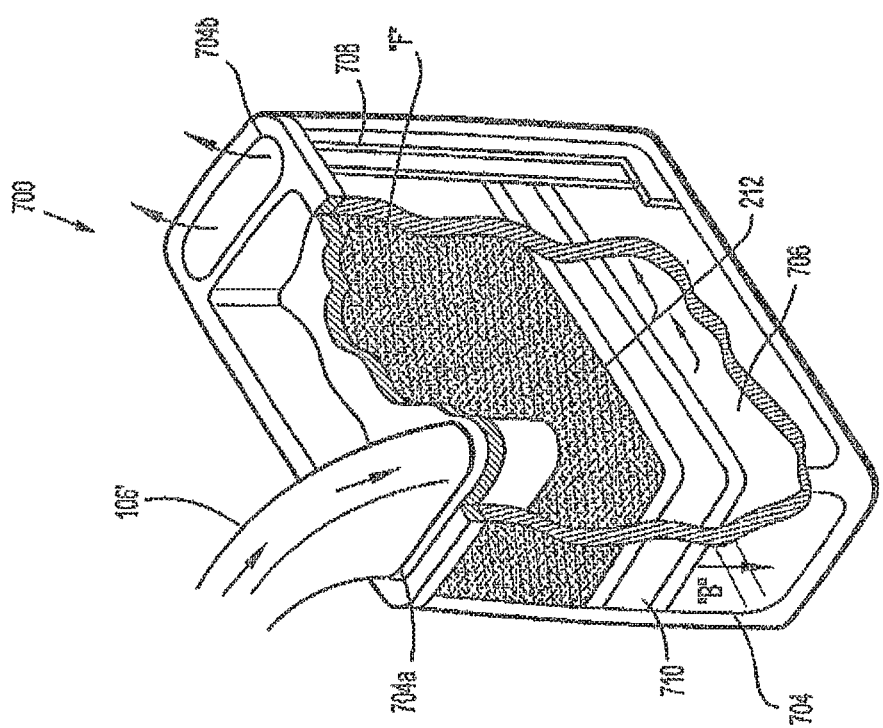
FIG. 9 is an interior perspective view of yet another embodiment of a collection canister according to the present disclosure.

Turning now to FIG. 9, another embodiment of the present disclosure is shown generally as collection device 700. Collection device 700 is substantially similar to collection device 600 and includes a container 704 having a first chamber 706 in fluid communication with a second chamber 708. First and second chambers 706, 708 are separated by a divider. An inlet port 704a fluidly communicates conduit 106' with first chamber 706. An outlet port 704b fluidly communicates second chamber 708 with a vacuum source (not shown). A plunger 710 is received within first chamber 706. Plunger 710 includes a hydrophobic membrane 212. Plunger 710 is configured to create a vacuum in first chamber 706 as plunger 710 is advanced in the direction of arrow "B". The vacuum in first chamber 706 causes fluid "F" to be drawn through conduit 106'. Once first chamber 706 is filled, conduit 106' is disconnected from container 704. Collection device 700 may include a valve or other mechanism (not shown) for draining container 704. Alternatively, collection device 700 may be discarded.

Figure 10A:
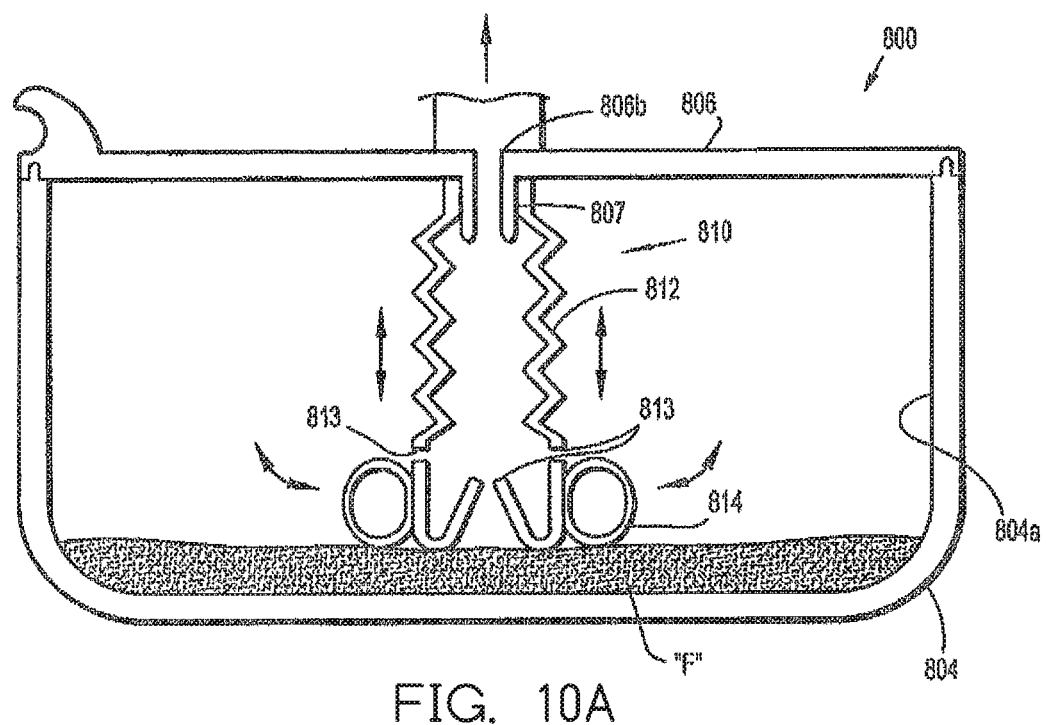
FIG. 10A is a cross-sectional side view of still another embodiment of a collection device according to the present disclosure.
Figure 10B:
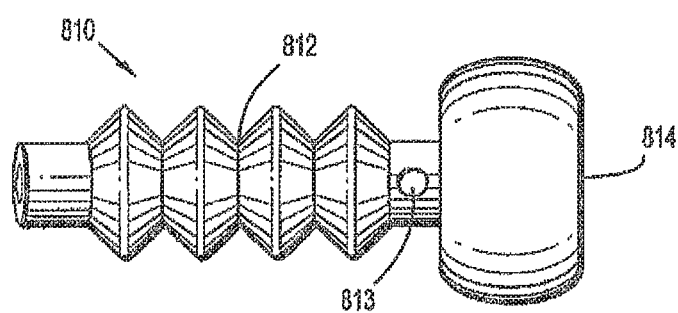
FIG. 10B is a side view of an intake mechanism of the collection device of FIG. 10A.

With reference now to FIGS. 10A and 10B, an alternate embodiment of the present disclosure is shown generally as collection canister 800. Collection device 800 includes a container 804 having a cover 806 and defining a substantially sealed chamber container 804a. An inlet port (not shown) may be formed in container 804 and/or cover 806. Cover 806 further includes an outlet port 806b configured for operable connection with a vacuum source. Cover 806 further includes a flange 807 extending inwardly from outlet port 806b. An intake mechanism 810 extends from flange 807 and is in fluid communication with outlet port 806b.

Intake mechanism 810 includes a bellows 812 and a float 814. Bellows 812 may be constructed of silicone or other suitable flexible material. Bellows 812 defines a passageway 812 therethrough in fluid communication with outlet port 806b. Bellows 812 includes openings 813 for receiving air from with chamber 804a. Float 814 may include an air bag, open cell material or other suitable material with a low mass. Float 814 may be affixed to an end of bellows 812. Alternatively, float 814 may be over-molded to bellows 812. Float 814 is configured to maintain at least one of openings 813 formed in bellows 812 above the level of fluid "F" as chamber 804a fills with fluid "F". Bellows 812 and float 814 are configured such that as container 804 is transported, i.e. tilted or inverted, collection device 800 continues to collect fluid "F".

Subatmospheric Pressure Mechanism for Wound Therapy System

Figure 11:
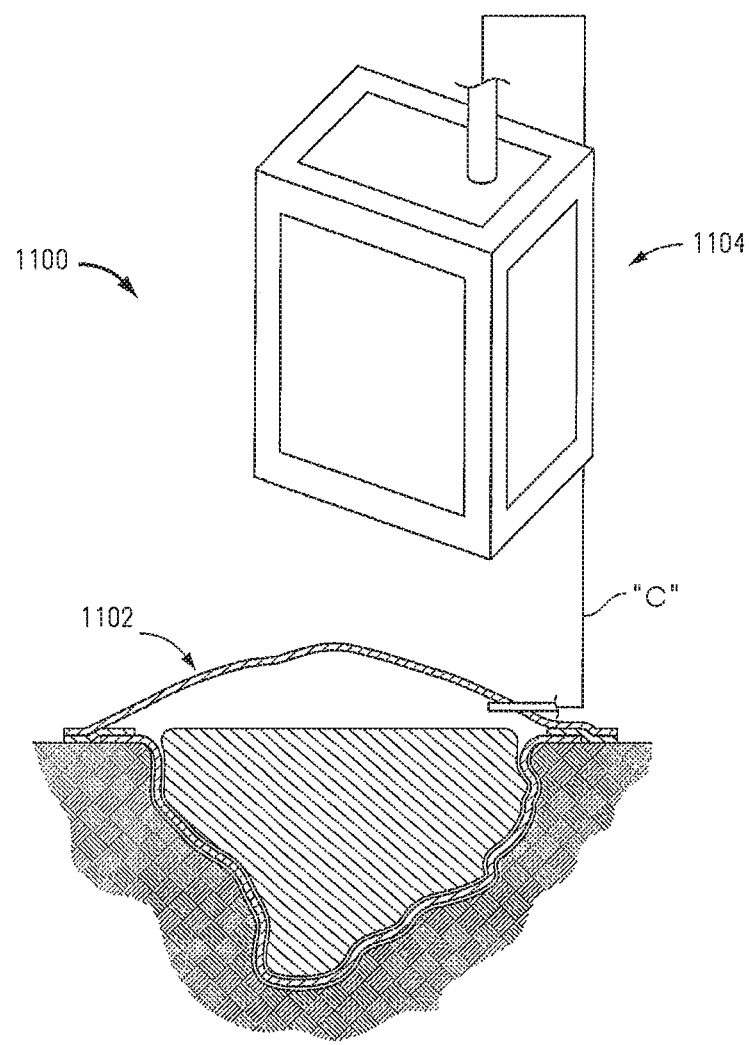
FIG. 11 is a view of a wound therapy system in accordance with the principles of the present disclosure.

Referring initially to FIG. 11, a wound therapy system of the present disclosure is shown generally as wound therapy system 1100. Wound therapy system 1100 includes composite wound dressing 1102 and subatmospheric pressure mechanism 1104 in fluid communication with the wound dressing 1102 through a conduit, identified schematically as reference character "c". For a more detailed description of wound dressing 1102, including the composition and operation thereof, please refer to commonly owned U.S. patent application Ser. No. 12/047,910, filed Mar. 13, 2008, the contents of which are incorporated herein by reference in their entirety.

Figure 12:
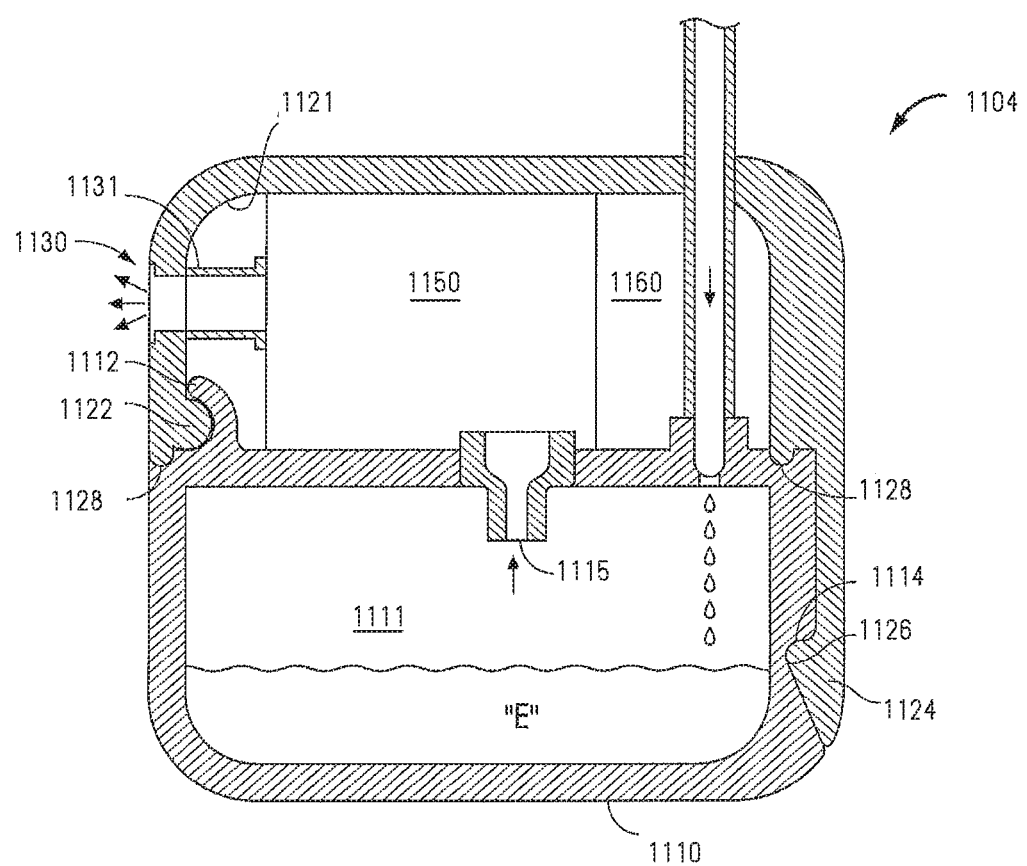
FIG. 12 is a side cross-sectional view of the subatmospheric pressure mechanism of the wound therapy system of FIG. 11.
Figure 13:
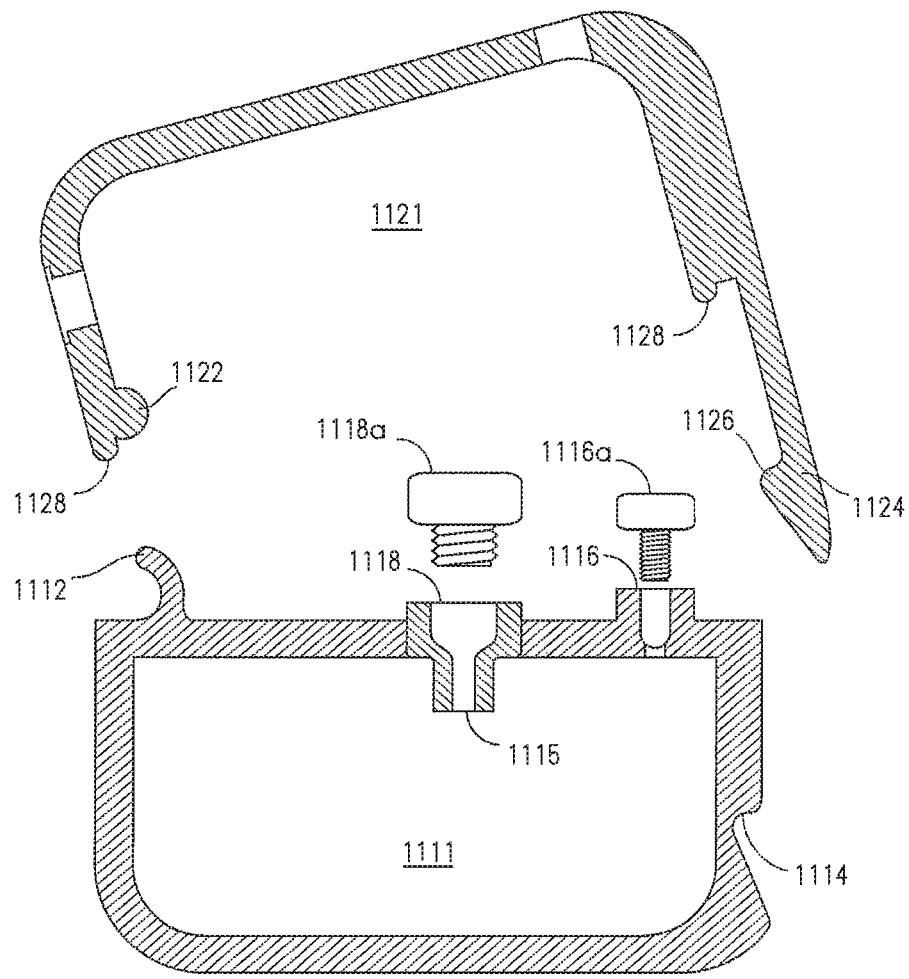
FIG. 13 is a side cross-sectional side view of the subatmospheric pressure mechanism of FIG. 12, illustrating the housing cover separated from the housing base.

With reference now to FIGS. 12-13, subatmospheric pressure mechanism 1104 will be described in detail. Subatmospheric pressure mechanism 1104 may be a portable canister adapted to be worn or carried by the subject via a strap, belt, or the like. In the alternative, pressure mechanism 1104 may be a component of a non-ambulatory system. Subatmospheric pressure mechanism 1104 includes housing base 1110 and housing cover 1120 selectively attachable to housing base 1110. Housing base 1110 and/or housing cover 1120 may be fabricated from substantially rigid material, or in the alternative, include a relatively flexible material. Housing base 1110 defines a first cavity 1111 for receiving fluid, e.g. exudates "E" from wound dressing 1102 (FIG. 11). Housing cover 1120 defines a second cavity 1121 to accommodate, e.g., a control unit for controlling operation of system 1100. The control unit may consist of vacuum source 1150, power source 1160, and logic software and/or processing means for controlling operation of vacuum source 1150 based on various parameters and/or in connection with a treatment regimen.

Housing base 1110 and housing cover 1120 may be adapted for releasable coupling. In one embodiment, housing base 1110 includes flange 1112 and notch or recess 1114. Flange 1112 is configured to engage lip 1122 formed in housing cover 1120. Notch 1114 is configured to selectively receive a tab 1126 of an extension 1124 of housing cover 1120. Housing base 1110 further includes a fluid inlet 1116 and a suction port 1118. Fluid inlet 1116 is configured to operably engage conduit "c" and may include a luer lock 1112a. Inlet 1116 is preferably configured to receive cap 1116a for preventing leakage of exudates "E" and odor from first cavity 1111 when housing cover 1120 is separated from housing base 1110. Suction port 1118 is configured to operably engage vacuum source 1150. Suction port 1118 may include a hydrophobic membrane or filter 1115 for preventing exudates "E" from being aspirated into vacuum source 1150. Suction port 1118 may also be configured to receive cap 1118a to prevent fluid leakage during disposal of housing base 1110.

With reference still to FIGS. 12 and 13, housing cover 1120 is configured for releasable engagement with housing base 1110 and includes second cavity 1121 for receiving vacuum source 1150 and power source 1160. Vacuum source 1150 and/or power source 1160 may be maintained with housing cover 1120 with rubber mounts (not shown) for reducing vibration within housing cover 1120. Housing cover 1120 may be constructed of and/or include STYROFOAM® or other sound dampening material. Housing cover 1120 may include an overlay, having lights and/or buttons (not shown) for monitoring and controlling the operation of subatmospheric pressure mechanism 1104. Housing cover 1120 includes lip 1122 configured to engage flange 1112 of housing base 1110. An extension 1124 extends from housing cover 1120 opposite lip 1122 and is configured for operable engagement by a user. Extension 1124 includes tab 1126 configured to engage notch 1114 formed in housing base 1110. Extension 1124 is configured to flex such that tab 1126 may be selectively received within notch 1114, thereby, releasably securing housing cover 1120 to housing base 1110. This snap-fit configuration may produce an audible sound when tab 1126 is received within notch 1114, thereby, notifying the user that housing cover 1120 and housing base 1110 are securely joined together.

Seal member 1128 extends about housing cover 1120 to form a seal between housing cover 1120 and housing base 1110 when housing cover 1120 is selectively secured to housing base 1110. Seal member 1128 may be secured to housing cover 1120 in any manner, including mechanical fastening, welding, and adhesive. Alternatively, seal member 1128 may extend about housing base 1110 to form a seal between housing base 1110 and housing cover 1120. In an alternative embodiment, seal member 1128 may include two or more seal elements (not shown). Seal member 1128 establishes and maintains a sealed relationship between cover 1120 and housing base 1110 when the components are assembled thereby preserving the integrity of the second cavity 1121 within cover 1120.

Figure 14A:
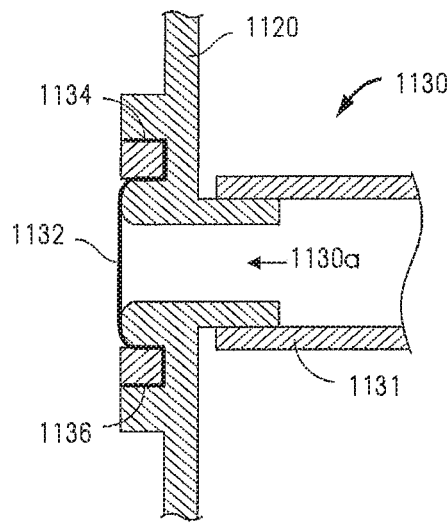
FIG. 14A is an enlarged side cross-sectional view of the vent assembly of the subatmospheric pressure mechanism of FIGS. 12 and 13.
Figure 14B:
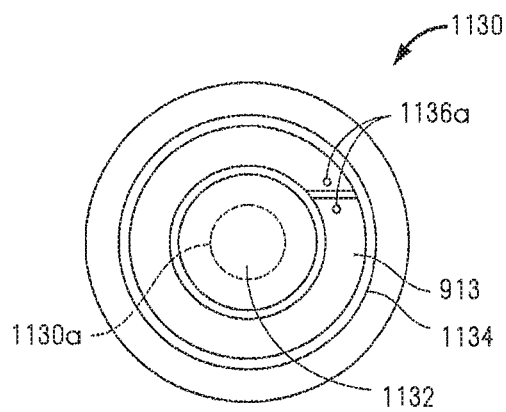
FIG. 14B is an enlarged plan view of the vent assembly of FIG. 14A.

Housing cover 1120 further includes vent assembly 1130 configured to vent exhaust air from vacuum source 1150 through exhaust port 1130a. Turning initially to FIGS. 14A and 14B, vent assembly 1130 extends from housing cover 1120 and is directly connected to vacuum source 1150 (FIG. 11) via tube 1131. Vent assembly 1130 includes filter 1132 extending across exhaust port 1130a and split ring 1136 for retaining filter 1132 over exhaust port 1130a. Vent assembly 1130 includes groove 1134 formed about exhaust port 1130a adapted to receive split ring 1136. Filter 1132 is sized and dimension such that an outer portion of filter 1132 folds into groove 1134 and is retained therein by split ring 1136. Filter 1132 may be hydrophobic in nature and/or may include charcoal or other odor absorbing material, and may prevent the passage of bacteria. Split ring 1136 may be formed of plastic, metal or other suitable material. Split ring 1136 may include openings 1136a configured to receive a tool for removing split ring 1136 from within groove 1134. In this manner, filter 1132 may be changed as necessary.

Figure 15A:
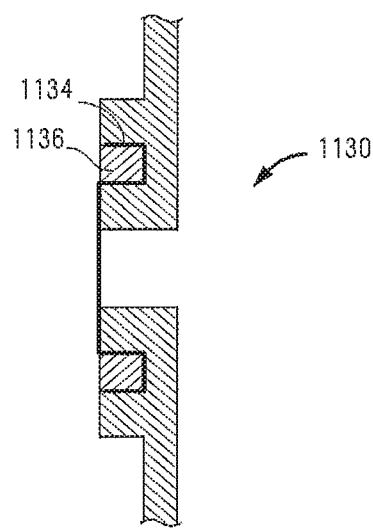
FIG. 15A is an enlarged side cross-sectional view of an alternate embodiment of the vent assembly of the subatmospheric pressure mechanism of FIGS. 12 and 13.
Figure 15B:
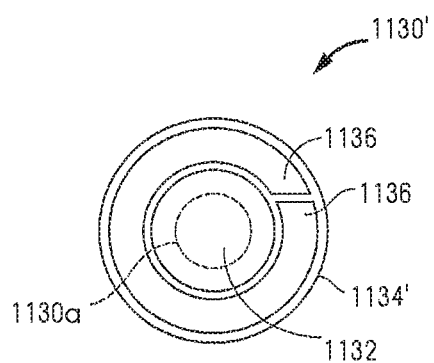
FIG. 15B is an enlarged front view of the vent assembly of FIG. 15A.

Turning now to FIGS. 15A and 15B, in an alternative embodiment, vent assembly 1130' may be recessed in housing cover 1120. Additionally, vent assembly 1130' may vent exhaust air from within second cavity 1121 rather than directly from vacuum source 1150 via tube 1131. In this manner, heat may be dissipated from within second cavity 1121 in addition to the venting of exhaust from vacuum source 1150. This configuration also provides a positive pressure on filter 1132. Filter 1132 is again retained within a groove 1134' formed in housing 1120 by split ring 1136.

In operation, subatmospheric pressure mechanism 1104 is adapted to draw exudates from wound dressing 1102 via conduit "c". Initially, housing cover 1120 is selectively secured to housing base 1110. To secure housing cover 1120 to housing base 1110, lip 1122 of housing cover 1120 is first received within flange 1112 of housing base 1110. Housing cover 1120 is then pivoted about flange 1112 such that extension 1124 received over housing base 1110. Housing cover 1120 is pivoted until tab 1126 of extension 1124 is received within notch 1114. Subatmospheric pressure mechanism 1104 may be configured such that receipt of tab 1126 within notch 1114 causes an audible sound, thereby confirming to a user that housing cover 1120 has been securely received on housing base 1110. Once subatmospheric pressure mechanism 1104 is assembled, conduit "'c'" may be fluidly coupled to fluid inlet 1116 and the control unit (not shown) may be activated. Activation of vacuum source 1150 creates suction within first cavity 1111 that draws exudates from wound dressing 1102 through conduit "c". Exudates "E" collect in first cavity 1111 of housing base 1110. Exhaust from vacuum source 1150 is vented either directly or indirectly through vent assembly 1130, 1130', respectively. Heat may also be dissipated through vent assembly 1130'.

Upon filling of first cavity 1111, completion of treatment or other any other reason, subatmospheric pressure mechanism 1104 may be deactivated and exudates "E" may be properly disposed. To disengage housing cover 1120 from housing base 1110, extension 1124 of housing cover 1120 is flexed away from housing base 1110. In this manner, tab 1126 on extension 1124 is withdrawn from engagement with notch 1114 formed in housing base 1110. Housing cover 1120 may be pivoted away from housing base 1110 until lip 1122 of housing cover 1120 disengages flange 1112 of housing base 1110. Once housing cover 1120 is separated from housing base 1110, exudates "E" may be disposed. Exudates "E" may be emptied from first cavity 1111, or alternatively, housing base 1110 may be disposed of in its entirety. In the event housing base 1110 is disposed, caps 1116a, 1118a may be placed in fluid inlet 1116 and suction port 1118, respectively, such that housing base 1110 may be transported without worry of fluid leakage or odor escaping from within cavity 1111.

Figure 16:
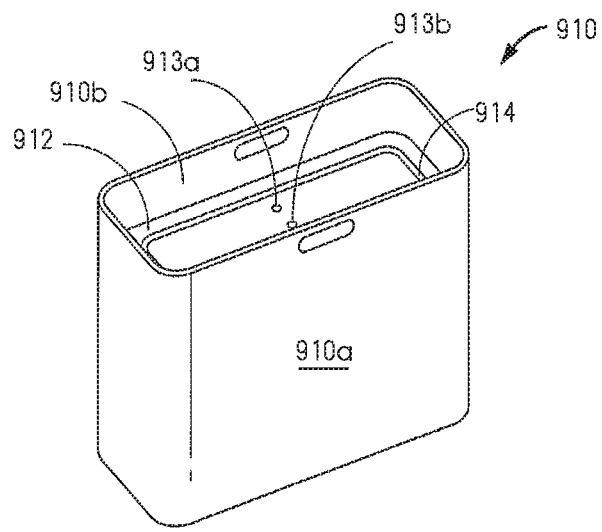
FIG. 16 is a perspective view of another subatmospheric pressure mechanism of the present disclosure.

With reference now to FIG. 16, a housing base of alternate embodiment of a subatmospheric pressure mechanism is shown as housing base 910. Housing base 910 includes divider 912 for separating housing base 910 into a fluid receiving portion 910a and an operational portion 910b configured for receiving a control unit, including a vacuum source and power source (not shown). Divider 912 includes a fluid inlet port 913a and a vacuum port 913b. Divider 912 further includes a gasket 914 extending about an outer periphery of divider 912. Gasket 914 is configured to engage vacuum source (FIG. 12) in a sealed manner, thereby enabling a vacuum to be created within fluid receiving portion 910a to draw fluid from wound dressing 1102 (FIG. 11).

Figure 17:
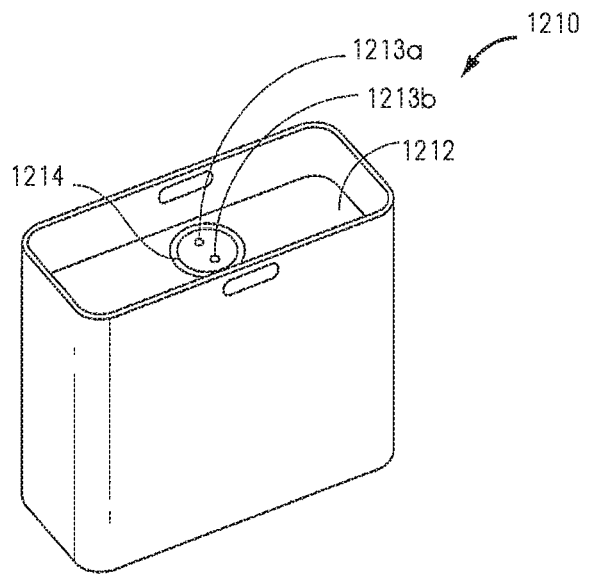
FIG. 17 is a perspective view of another embodiment of the subatmospheric pressure mechanism.

Turning now to FIG. 17, a housing base of an alternative embodiment of the subatmospheric pressure mechanism of the present disclosure is shown generally as housing base 1210. Subatmospheric pressure mechanism 1210 includes a divider 1212 including a fluid inlet port 1213a and vacuum port 1213b. Divider 1212 further includes a gasket 1214 extending about fluid inlet port 1213a and vacuum port 1213b for engaging a vacuum source (FIG. 12) in a sealed manner. By localizing gasket 1214 around fluid inlet port 1213a and vacuum port 1213b the likelihood of scaling issues, such as air and fluid leaks, is reduced. Gasket 1214 may be formed of gel or other suitable sealing material. One preferred gel material is a silica gel.

Figure 18:
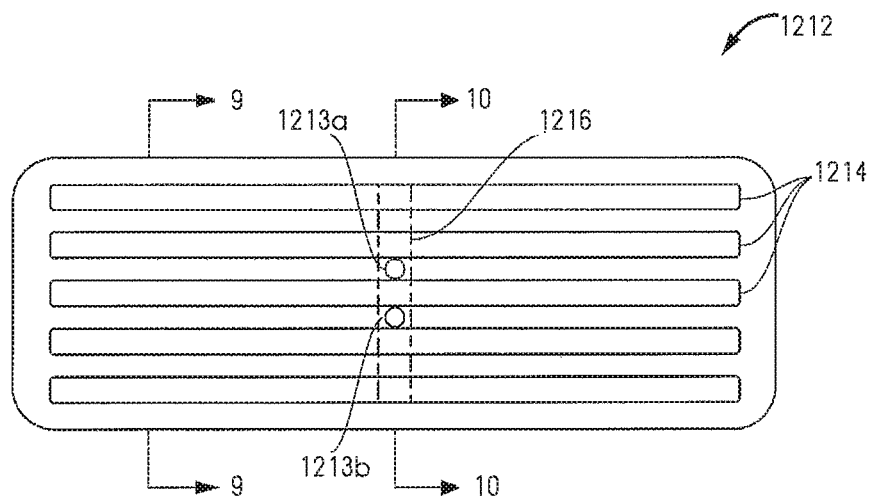
FIG. 18 is a plan view of the divider of the subatmospheric pressure mechanism of FIG. 17.
Figure 19:
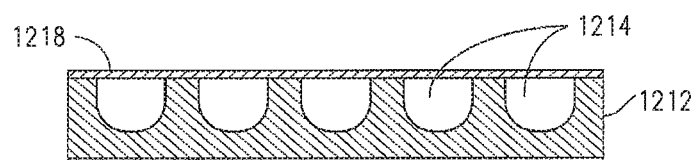
FIG. 19 is cross-sectional end view of the divider of FIG. 18 taken along line 9-9.
Figure 20:
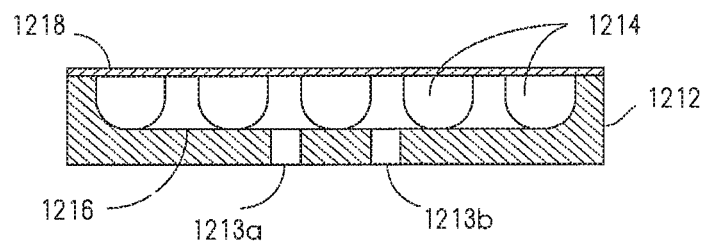
FIG. 20 is a cross sectional view of the divider of FIG. 18 taken along line 10-10.

With reference now to FIGS. 18-20, underside 1212a of divider 1212 is configured to assist in fluid collection. Divider 1212 includes a plurality of longitudinal grooves 1214 extending the length thereof. Channel 1216 extends the width of divider 1212 in alignment with fluid inlet port 1213a and vacuum port 1213b. Channel 1216 fluidly communicates each of the plurality of longitudinal grooves 1214 with fluid inlet port 1213a and vacuum port 1213b. Divider 1212 may be integrally fanned with housing base 1210, or as shown configured to be received within housing base 1210. In this manner, divider 1212 is sealed within housing base 1210 using a hydrophobic adhesive or other suitable bonding material (not shown). Divider 1212 may further include a hydrophobic membrane 1218 at least partially covering longitudinal grooves and vacuum port 1213b. Hydrophobic membrane 1216 provides a fluid barrier between the fluid collection chamber and the control mechanism. Longitudinal grooves 1214 provide increased surface area for air flow through hydrophobic membrane 1218. This may assist vacuum flow, e.g., in the event that a portion of the surface area becomes clogged and/or covered with exudate "E" or other fluid.

Canister Membrane for Wound Therapy System

The hydrophobic membranes of the disclosure will be discussed in connection with use in a wound therapy system applying subatmospheric pressure for promoting healing of a wound. Although the membranes will be described as relates to a wound therapy system, alternative uses for the membranes are envisioned. The wound therapy system includes a wound dressing and a portable subatmospheric pressure mechanism in fluid communication with the wound dressing. The subatmospheric pressure mechanism applies subatmospheric pressure to the wound to effectively remove wound fluids or exudates captured by the composite wound dressing, and to increase blood flow to the wound bed, thereby enhancing cellular stimulation of epithelial and subcutaneous tissue. The wound therapy system may be entirely portable, i.e., it may be worn or carried by the subject such that the subject may be completely ambulatory during the therapy period. The wound therapy system may be entirely disposable after a predetermined period of use or may be individually disposable whereby some of the components are reused for a subsequent therapy application.

Figure 21:
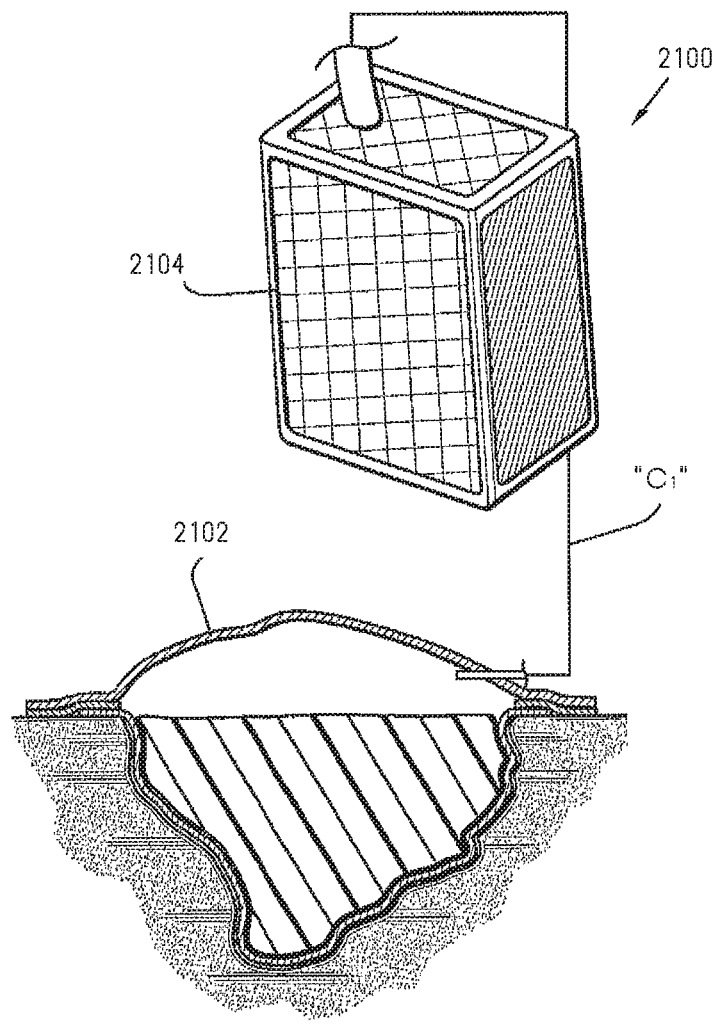
FIG. 21 is a perspective view of a portable wound therapy system.

Referring initially to FIG. 21, wound therapy system 2100 is illustrated. Wound therapy system 2100 includes composite wound dressing 2102 and subatmospheric pressure mechanism or collection canister 2104 in fluid communication with the wound dressing 2102 through a conduit, identified schematically as reference character "$c_1$". For a more detailed description of wound dressing 2102, including the composition and operation thereof, please refer to commonly assigned U.S. patent application Ser. No. 11/825,480, filed Jul. 6, 2007, the contents of which are incorporated herein by reference in their entirety.

With reference now to FIGS. 22A-22C, the structure and operation of collection canister 2104 will be described as it relates to the wound therapy system 2100. Canister 2104 includes housing 2106 defining first chamber 2106a and second chamber 2106b. Housing 2106 may be rigid, or, in the alternative, comprise a flexible material. First chamber 2106a includes vacuum source 2150 and power source 2160. Vacuum source 2150 may be any suitable vacuum pump adapted to present negative pressure either continuously or intermittently within wound dressing 2102. Vacuum source 2150 may be associated with computer logic, software or processing means to control operation of therapy system 2100.

Second chamber 2106b of canister 2104 defines a fluid receiving cavity for receiving exudates and/or fluid "$F_1$" from wound dressing 2102 (FIG. 21). First and second chambers 2106a, 2106b are separated by divider 2108. Divider 2108 includes hydrophobic membrane 2110 adapted to prevent aspiration of fluid "$F_1$" collected in second chamber 2106b into vacuum source 2150. Container 2104 further includes cover 2107 positioned to seal second chamber 2106a. Conduit "$c_1$" extends through cover 2107 and divider 2108 and terminates adjacent an upper area or section of canister 2104.

With continued reference to FIGS. 22A-22C, divider 2108 includes opening 2108a for receiving conduit "$c_1$" therethrough, and rectangular opening 2108b for at least partially receiving hydrophobic membrane 2110. Although a rectangular opening 2108b is depicted, other shapes for hydrophobic membrane 2110 and opening 2108b are envisioned. Opening 2108a may define the outlet of vacuum source 2150 which draws a vacuum within second chamber 2106b. Although the rectangular opening is 2108b implies a hole or void, this opening may consist of a screen, mesh, or grill to provide structural support to the hydrophobic membrane 2110 while still allowing air flow through the membrane.

Hydrophobic membrane 2110 spans a substantially large surface area or cross-section of canister 2104 relative to conventional filters which typically cover a small opening adjacent the vacuum pump. Accordingly, as depicted in FIGS. 23B-23C, when canister 2104 is tilted or placed on one of its sides 2115, unless the canister 2104 is substantially full with fluids "$F_1$" or exudates, at least a portion of hydrophobic membrane 2110 will remain free of fluid thereby permitting continued vacuum draw through hydrophobic membrane 2110, divider 2108 and within canister 2104. Thus, the relatively large surface area of hydrophobic membrane 2110 enables continued use of system 2100 even when canister 2104 is positioned on its side 2115 or tilted. In one aspect, hydrophobic membrane 2110 encompasses at least seventy-five (75%) percent of the cross-section of canister 2104 and has a length and width closely approximating the respective length and width of "$L_1$, $W_1$. In one embodiment, hydrophobic membrane 2110 defines a length "$L_1$" and a width "$W_1$" ranging from about 65%-90% the respective length "$L_0$" and width "$W_0$" of canister 2104.

Once hydrophobic membrane 2110 is completely covered by fluid "$F_1$", in the event second chamber 2106b is near capacity and canister 2104 is placed on either side 2115, or when second chamber 2106b is completely full, vacuum source 2150 may no longer draw air through hydrophobic membrane 2110. Once air can no longer be drawn through hydrophobic membrane 2110, the suction drawing fluid "$F_1$" from wound dressing 2102 is ceased and fluids "$F_1$" are no longer drawn into second chamber 2106b. Canister 2104 then may be emptied or replaced, and therapy may be continued.

Figure 24:
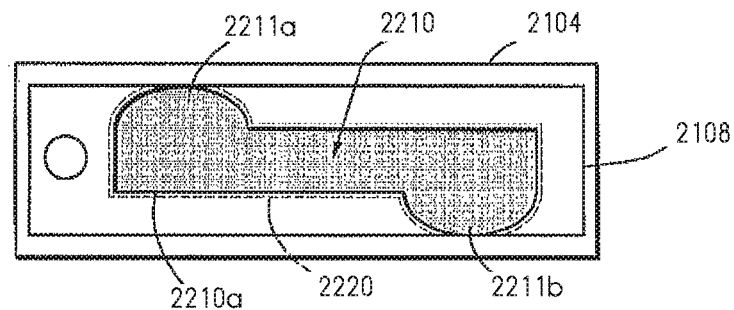
FIG. 24 is top view of a collection canister including an alternate embodiment of a hydrophobic membrane in accordance with an aspect of the present disclosure.
Figure 25:
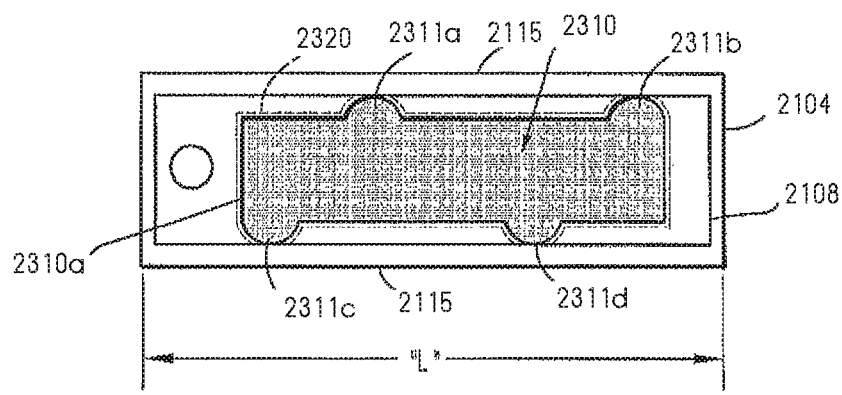
FIG. 25 is top view of a collection canister including another alternate embodiment of a hydrophobic membrane in accordance with an aspect of the present disclosure.
Figure 26:
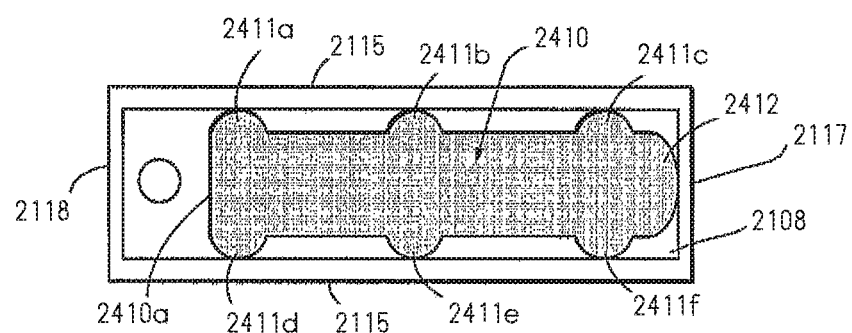
FIG. 26 is top view of a collection canister including another embodiment of a hydrophobic membrane in accordance with an aspect of the present disclosure.

With reference now to FIGS. 24-26, other embodiments of collection canisters including hydrophobic membranes according to the present disclosure will now be described and are shown generally as hydrophobic membranes 2210, 2310, 2410. Each of hydrophobic membranes 2210, 2310, 2410 is configured to maximize the effective working area of the membrane to maintain the vacuum draw during manipulation or transfer of the ambulatory system. Each of hydrophobic membranes 2210, 2310, 2410 is securely received within, or mounted to, divider 2108.

Referring initially to FIG. 24, hydrophobic membrane 2210 defines a substantially rectangular body 2210a including opposing first and second lobes 2211a, 2211b extending outwardly along a length thereof. For example, hydrophobic membrane 2210 may define a substantially Z-shaped member. Divider 2108 may have a corresponding inner wall defining a complementary Z-shaped opening 2220 (shown in phantom) for at least partially accommodating hydrophobic membrane 2210. Opening 2220 follows the contour of the periphery of hydrophobic membrane 2210. Although the opening 2220 implies a hole or void, this opening may consist of a screen, mesh, or grill to provide structural support to the hydrophobic membrane 2210 while still allowing air flow through the membrane 2210.

Hydrophobic membrane 2210 is adapted to permit air flow when canister 2104 is in an upright position, tilted position or on either side 2115. In particular, the positioning of lobes 2211a, 2211b in opposed relation both vertically and horizontally with respect to FIG. 24 increases the possibility that one of the lobes 2211a, 2211b will be free of, or not covered by, liquid when canister 2104 is tilted or placed on its side thereby permitting continued vacuum draw within canister 2104. Lobes 2211a, 2211b may be dimensioned to extend substantially to side wall 2115 of canister 2104 to maximize the effective operating area of hydrophobic membrane 2210.

Referring now to FIG. 25, this embodiment of hydrophobic membrane 2310 includes a body 2310a having multiple outwardly extending lobes 2311a, 2311b, 2311c, 2311d staggered along the length "L". Hydrophobic membrane 2310 may include any number of lobes 2311a, 2311b, 2311c, 2311d. As with lobes 2211a, 2211b, lobes 2311a, 2311b, 2311c, 2311d permit air to flow through hydrophobic membrane 2310 when canister 2104 is in an upright or tilted position. The additional lobes 2311a, 2311b, 2311c, 2311d along the length of rectangular body 2310a may enhance vacuum flow through hydrophobic membrane 2310. Divider 2108 may include a correspondingly shaped opening 2320 (shown in phantom) for receiving membrane 2310. It is envisioned that divider 2108 may include ribbing or other structural support between lobes 2311a, 2311b, 2311c, 2311d to reinforce hydrophobic membrane 2310 and/or to add structural integrity to canister 2104.

With reference now to FIG. 26, another embodiment of hydrophobic membrane 2410 is illustrated. Hydrophobic membrane 2410 includes a body 2410a having multiple opposing lobes 2411a, 2411b, 2411c, 2411d extending outwardly along a length thereof. Hydrophobic membrane 2410 further includes lobe 2412 which extends to end wall 2117 of canister 2104. As with hydrophobic membranes 2210, 2310, lobes 2411a, 2411b, 2411c, 2411d permit air to flow through hydrophobic membrane 2410 when canister 2104 is in an upright position, tilted position or positioned on one of its sides 2115. In addition, lobe 2412 further permits air to flow through hydrophobic membrane 2410 if canister 2104 is positioned on opposed end wall 2118. In particular, when canister 2104 is positioned on end wall 2118, a volume of air will be present adjacent end wall 2117 (provided canister 2104 is not full with fluids "$F_1$") to permit continued vacuum draw through lobe 2412 and into second chamber 2106b of canister 2104.

Figure 27:
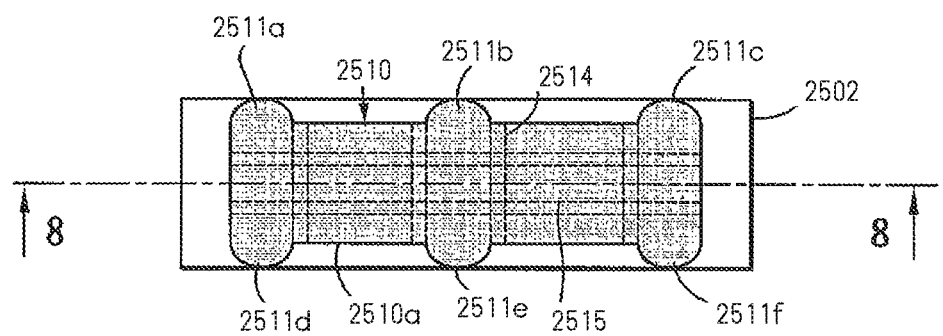
FIG. 27 is top view of another embodiment of a hydrophobic membrane in accordance with an aspect of the present disclosure.
Figure 28:
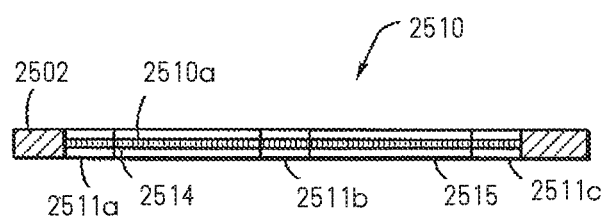
FIG. 28 is a cross-sectional side view of the hydrophobic membrane of FIG. 27.

Referring now to FIGS. 27 and 28, another alternate embodiment of according to the present disclosure is illustrated. Filter assembly 2510 is independent of canister 2104 (FIG. 21) and may be releasably mounted within canister 2104 by conventional means. Filter assembly 2510 may be disposed after use if desired and replaced with a new filter assembly 2510 which may be mounted within canister 2104. Filter assembly 2510 includes base 2502 and filter element 2512 within the base 2502. Base 2502 defines a substantially planar member configured to be received in a fluid collection canister (not shown). Base 2502 may be adapted for selective attachment with or permanently fixed to the collection canister 2104. Filter membrane 2512 defines a substantially rectangular area and possesses multiple opposing lobes 2511a, 2511b, 2511c, 2511d, 2511e, 2511f extending outwardly along a length thereof. Additional lobes 2516 (shown in phantom) may be provided adjacent the end of filter membrane 2512. Base 2502 may further include lateral and longitudinal supports 2514, 2515 extending across the width and length of hydrophobic membrane 2510, respectively. Filter membrane 2512 functions in a similar manner to the filter membranes described in connection with the prior embodiments by increasing the overall effective operable area of the filter to permit vacuum draw in the event of tipping or inversion of canister 2104.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A negative pressure wound therapy system comprising:
   a wound dressing dimensioned for positioning relative to a wound bed of a subject; and,
   a subatmospheric pressure mechanism configured to aspirate fluid from a wound, the subatmospheric pressure mechanism comprising:
   a canister configured to receive exudates from the wound bed; and
   a divider having a plurality of longitudinal grooves formed on an underside thereof,
   wherein the canister has a fluid inlet port and a vacuum port, the fluid inlet port being configured for fluid communication with the wound dressing.

2. The system of claim 1, wherein at least one of the fluid inlet port and the vacuum port are configured to receive a cap.

3. The system of claim 1, wherein the divider further includes a channel fluidly communicating the plurality of longitudinal grooves with at least one of the fluid inlet port and the vacuum port.

4. The system of claim 1, wherein the canister has a first subatmospheric pressure mechanism chamber and a second fluid chamber for collecting fluids removed from the wound dressing, the canister further including a hydrophobic membrane separating the first subatmospheric pressure mechanism chamber and the second fluid chamber.

5. The system of claim 4, wherein the hydrophobic membrane at least partially covers the plurality of longitudinal grooves.

\* \* \* \* \*